US010500386B2

(12) United States Patent
Tamaru et al.

(10) Patent No.: US 10,500,386 B2
(45) Date of Patent: Dec. 10, 2019

(54) MICRONEEDLE ARRAY MANUFACTURING METHOD

(71) Applicants: ASTI CORPORATION, Hamamatsu-shi, Shizuoka (JP); TAKEDA PHARMACEUTICAL COMPANY LIMITED, Osaka-shi, Osaka (JP)

(72) Inventors: Takuya Tamaru, Hamamatsu (JP); Noriyuki Ogai, Hamamatsu (JP); Akifumi Inoue, Hamamatsu (JP); Sigeru Tomita, Osaka (JP); Ikuhiko Wada, Osaka (JP)

(73) Assignees: ASTI CORPORATION, Hamamatsu-Shi, Shizuoka (JP); TAKEDA PHARMACEUTICAL COMPANY LIMITED, Osaka-Shi, Osaka (JP)

( * ) Notice: Subject to any disclaimer, the term of this patent is extended or adjusted under 35 U.S.C. 154(b) by 583 days.

(21) Appl. No.: 14/908,394

(22) PCT Filed: Jul. 29, 2014

(86) PCT No.: PCT/JP2014/069983
§ 371 (c)(1),
(2) Date: Jan. 28, 2016

(87) PCT Pub. No.: WO2015/016235
PCT Pub. Date: Feb. 5, 2015

(65) Prior Publication Data
US 2016/0158512 A1 Jun. 9, 2016

(30) Foreign Application Priority Data

Jul. 30, 2013 (JP) ................................ 2013-157329

(51) Int. Cl.
B29C 39/10 (2006.01)
A61M 37/00 (2006.01)
B29L 31/00 (2006.01)

(52) U.S. Cl.
CPC ......... *A61M 37/0015* (2013.01); *B29C 39/10* (2013.01); *A61M 2037/0023* (2013.01);
(Continued)

(58) Field of Classification Search
None
See application file for complete search history.

(56) References Cited

U.S. PATENT DOCUMENTS

RE25,560 E * 4/1964 Gilford .................... 264/264
4,956,139 A * 9/1990 Koizumi ........... B29C 45/14221
264/154

(Continued)

FOREIGN PATENT DOCUMENTS

EP 1590034 A1 11/2005
EP 2062612 A1 5/2009
(Continued)

OTHER PUBLICATIONS

Europe Patent Office, "Search Report for European Patent Application No. 14832762.0," Mar. 10, 2017.
(Continued)

*Primary Examiner* — Edmund H Lee
(74) *Attorney, Agent, or Firm* — Manabu Kanesaka

(57) ABSTRACT

The purpose of the present invention is to provide: a microneedle array that does not readily break during puncture and thereby improves the reliability of puncturing, the microneedle array being capable of administering the desired amount of the target substance; and a microneedle manufacturing method for manufacturing a microneedle array of such description. To achieve the above purpose, the
(Continued)

invention is characterized in being provided with: a substrate; a plurality of microneedle base sections formed integrally in a protruding manner on the substrate; and microneedle end sections installed at the ends of the microneedle base sections to form microneedles and provided with in vivo solubility or biodegradability, the microneedle end sections holding the target substance, a recess for admitting the microneedle end sections being provided to the microneedle base sections, and a part of the microneedle end sections being admitted into the recess for admitting the microneedle end sections.

8 Claims, 22 Drawing Sheets

(52) U.S. Cl.
CPC . *A61M 2037/0053* (2013.01); *A61M 2205/02* (2013.01); *B29L 2031/7544* (2013.01)

(56) References Cited

U.S. PATENT DOCUMENTS

| | | |
|---|---|---|
| 8,506,980 B2 | 8/2013 | Takada |
| 9,289,925 B2 | 3/2016 | Ferguson et al. |
| 2002/0133129 A1 | 9/2002 | Arias et al. |
| 2004/0106904 A1 | 6/2004 | Gonnelli et al. |
| 2008/0208134 A1 | 8/2008 | Tomono |
| 2008/0269670 A1 | 10/2008 | Kingsford |
| 2010/0280457 A1 | 11/2010 | Tokumoto et al. |
| 2011/0046575 A1 | 2/2011 | Takada |
| 2012/0041412 A1 | 2/2012 | Roth et al. |
| 2012/0265145 A1 | 10/2012 | Mefti et al. |
| 2013/0046244 A1 | 2/2013 | Kinuta |

FOREIGN PATENT DOCUMENTS

| | | |
|---|---|---|
| JP | H05-206084 A | 8/1993 |
| JP | H07-040357 A | 2/1995 |
| JP | 2004-526581 A | 9/2004 |
| JP | 2007-069915 A | 3/2007 |
| JP | 2011-206178 A | 10/2011 |
| JP | 2013-032324 A | 2/2013 |
| JP | 2013-094224 A | 5/2013 |
| JP | 2013-515524 A | 5/2013 |
| JP | 2013-517907 A | 5/2013 |
| WO | 2006/080508 A1 | 8/2006 |
| WO | 2008/020633 A1 | 2/2008 |
| WO | 2008/139648 A1 | 11/2008 |
| WO | 2010/117602 A2 | 10/2010 |
| WO | 2011/138917 A1 | 11/2011 |

OTHER PUBLICATIONS

PCT/ISA/210, "International Search Report for International Application No. PCT/JP2014/069983," Aug. 26, 2014.

Chu, L. Y. et al., "Separable arrowhead microneedles," Journal of Controlled Release, 2011, p. 242-249, vol. 149, Elsevier B.V.

\* cited by examiner

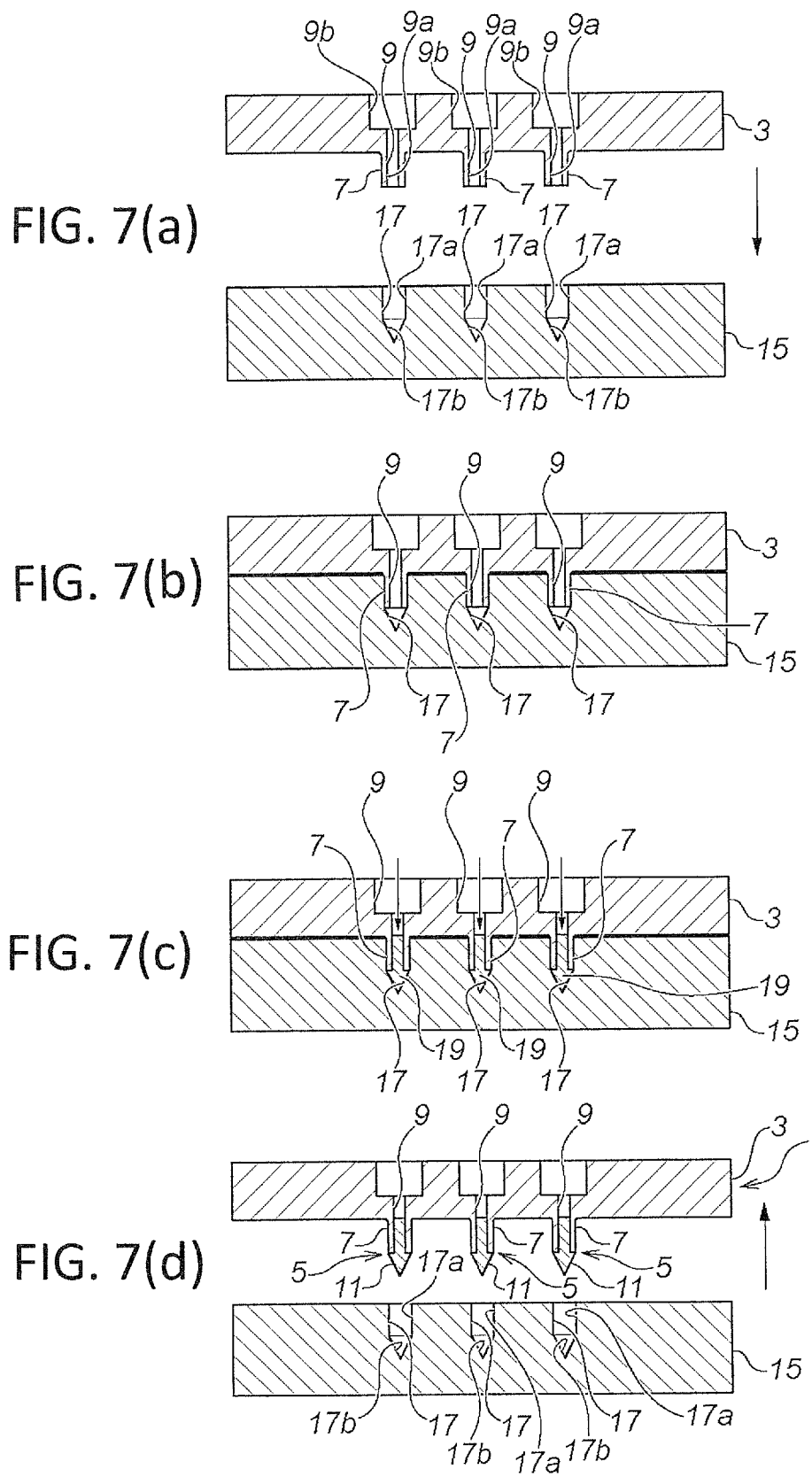

MICRONEEDLE ARRAY MANUFACTURING METHOD

RELATED APPLICATIONS

The present application is National Phase of International Application No. PCT/JP2014/069983 filed Jul. 29, 2014, and claims priority from Japanese Application No. 2013-157329, filed Jul. 30, 2013, the disclosure of which is hereby incorporated by reference herein in its entirety.

TECHNICAL FIELD

The present invention relates to a microneedle array for performing subcutaneous administration of an objective substance such as medical agent for the purposes of prevention and treatment of various diseases, and a microneedle array manufacturing method for manufacturing such a microneedle array, and more specifically, relates to that which is not easily damaged during puncturing, whereby the puncturing can be surely performed, and a desired volume of the objective substance can be surely administrated.

BACKGROUND ART

As examples of conventional microneedle arrays, those as described in Patent Document 1 and Patent Document 2 are known.

A percutaneous absorption formulation holding sheet (microneedle array) described in Patent Document 1 has a structure as illustrated in FIG. 33. There is a support body 1001, and percutaneous absorption formulations (microneedles) 1003, each of which is substantially in a conical fine needle shape, are firmly fixed on the support body 1001. The percutaneous absorption formulations 1003 are punctured into the skin.

Moreover, Patent Document 1 also discloses a percutaneous absorption formulation holding tool. The percutaneous absorption formulation holding tool is composed of a main body having penetration holes, and percutaneous absorption formulations, each of which is in a needle shape and held inside the respective penetration hole.

Moreover, a percutaneous administration formulation (a microneedle array) described in Patent Document 2 has a structure as illustrated in FIG. 34. There is a support body 1005, and a plurality of fine needles (microneedles) 1007 is firmly fixed on the support body 1005. The fine needle 1007 is substantially in a conical shape, composed of a first portion 1009 on the top end side (the upper side of FIG. 34) and a second portion 1011 on the base end side (the lower side of FIG. 34). The first portion 1009 was prepared, for example, by mixing a base, which is comprising a high-molecular substance having an in vivo solubility and a thread-forming property, with an objective substance such as a local anesthetic medicine and water, and thereafter, by drying and solidifying thereof. Moreover, the second portion 1011 was prepared, for example, by mixing a base, comprising a high-molecular substance having an in vivo solubility and a thread-forming property, with water, and thereafter, by drying and solidifying thereof.

On the other hand, by using a metallic base part, there is also a development of a microneedle medical formulation, having a biodegradable substance containing an objective substance at the tip part thereof (Non-Patent Document 1).

Further, there are various developments of safe medical formulations by which a desired volume of the objective substance can be administrated more surely.

REFERENCE DOCUMENTS OF CONVENTIONAL ART

Patent Document(s)

Patent Document 1: Pamphlet of International Publication 06/080508.
Patent Document 2: Official Gazette, JP 2013-32324 A.

Non-Patent Document(s)

Non-Patent Document 1; Leonard Y. Chu, Mark R. Prausnitz, "Separable Arrowhead Microneedles" (Journal of Controlled Release, 2011, Vol. 149, pp. 242-249).

SUMMARY OF THE INVENTION

Problems to be Solved by Invention

However, the above structures of the prior arts have the following problems:

First, in the case of the percutaneous absorption formulation holding sheet as described in Patent Document 1, since the percutaneous absorption formulation 1003, which has been manufactured separately, is fixed on the support body 1001, the strength thereof is not sufficient, and in particular, the strength of the fixed part is insufficient. Therefore, when attempting to puncture into the skin, depending on the method of puncturing (for example, when punctured obliquely against the skin), there may be a problem that the percutaneous absorption formulation 1003 is damaged to be broken from the fixed part, and the puncturing cannot be performed surely.

Moreover, there is another problem that, when the percutaneous absorption formulation 1003 is damaged during puncturing, the objective substance cannot be administrated at a desired volume.

Moreover, also in the case of the percutaneous administration formulation as described in Patent Document 2, since the second portion 1011 of the fine needle 1007, which has been manufactured separately, is fixed on the support body 1005, the strength thereof is not sufficient, and falls down from the bottom during puncturing into the skin, and the puncturing cannot be performed surely.

Moreover, since the percutaneous administration formulation is formed by using a female mold, when the finished percutaneous administration formulation is removed from the female mold, there may be a problem that the fine needle 1007 is bent from the bottom, or damaged.

Moreover, these problems are common to the first portion 1009 containing the objective substance such as a local anesthetic medicine. Since there is a boundary facing the second portion 1011, the strength thereof is not sufficient, and there may be problems of causing damages thereto and not being able to administrate a desired volume of the objective substance.

Moreover, as is common to the percutaneous adsorption formulation 1003 of Patent Document 1, the fine needle 1007 is in a conical shape, of which cross-section area increases gradually from the top end side toward the base end side, and therefore, when reaching more than a certain depth, the puncturing becomes difficult, and also needle slips out easily.

In the light of the above problems, it is an object of the present invention to provide a microneedle array, which is not easily damaged during puncturing, whereby the puncturing can be performed surely, and a desired volume of the objective substance can be administrated surely, and also, to provide a microneedle array manufacturing method to manufacture such a microneedle array.

Means to Solve the Problem

To achieve the objects mentioned above, a microneedle array of a mode (1) of the present invention is comprising: a substrate; a plurality of microneedle base parts protrusively formed on the substrate integrally; and a microneedle tip part installed on the top of each of the plurality of microneedle base parts, respectively, so as to constitute a microneedle, provided with in vivo solubility and biodegradability, and holding an objective substance, and is characterized in that: a microneedle tip part intrusion recess is formed in the microneedle base part; and the microneedle tip part partially intrudes into the microneedle tip part intrusion recess.

Moreover, the microneedle array of a mode (2) is characterized in that, with reference to the microneedle array of the mode (1), the microneedle tip part intrusion recess is penetration hole or groove.

Moreover, the microneedle array of a mode (3) is characterized in that, with reference to the microneedle array of the mode (1) or the mode (2), the plurality of microneedles is punctured into the skin and is then pulled out, so that the microneedle tip parts remain under the skin.

Moreover, the microneedle array of a mode (4) is characterized in that, with reference to the microneedle array of any of the mode (1) to the mode (3), the microneedle tip part is provided with a perpendicular part.

Moreover, the microneedle array of a mode (5) is characterized in that, with reference to the microneedle array of the mode (4), an uneven part is formed in the perpendicular part of the microneedle tip part.

Moreover, the microneedle array of a mode (6) is characterized in that, with reference to the microneedle array of any of the mode (1) to the mode (5), the cross sections of the microneedle base part and the microneedle tip part are rectangle.

Moreover, the microneedle array of a mode (7) is characterized in that, with reference to the microneedle array of any of the mode (1) to the mode (6), a protrusion is formed on the microneedle base part on the side of the microneedle tip part, and the microneedle tip part is installed on the microneedle base part so as to cover the protrusion.

Moreover, the microneedle array of a mode (8) is characterized in that, with reference to the microneedle array of any of the mode (1) to the mode (7), the substrate and the microneedle base parts are made of resin.

Moreover, the microneedle array of a mode (9) is characterized in that, with reference to the microneedle array of the mode (8), the resin is a biocompatible resin.

Moreover, the microneedle array of a mode (10) is characterized in that, with reference to the microneedle array of the mode (8), the resin is a biodegradable resin.

Moreover, the microneedle array of a mode (11) is characterized in that, with reference to the microneedle array of the mode (8), the resin is an in vivo insoluble resin.

Moreover, the microneedle array of a mode (12) is characterized in that, with reference to the microneedle array of any of the mode (1) to the mode (11), a barb is formed in the microneedle tip part.

Moreover, a microneedle array manufacturing method of a mode (13) is characterized in that: a female mold provided with microneedle forming recesses is prepared, and also a substrate, having an integrally formed plurality of microneedle base parts each of which provided with a microneedle tip part intrusion recess formed therein, is prepared; the substrate is installed in the female mold so that the plurality of microneedle base parts is fitted into the microneedle forming recesses; a dissolved or melted material, constituting a microneedle tip part and containing an objective substance, is filled in the microneedle forming recess, so that the filled material partially intrude into the microneedle tip part intrusion recess; and after expiration of a predetermined curing, the substrate is removed from the female mold, so that the microneedle array, having the microneedle tip part installed on the top of each of the plurality of the microneedle base parts of the substrate, is obtained.

Moreover, a microneedle array manufacturing method of a mode (14) is characterized in that: a female mold provided with microneedle forming recesses is prepared, and also a substrate, having an integrally formed plurality of microneedle base parts each of which provided with a microneedle tip part intrusion recess formed therein, is prepared; a dissolved or melted material, constituting a microneedle tip part and containing an objective substance, is filled in the microneedle forming recess; the substrate is installed in the female mold, so that, the plurality of microneedle base parts is fitted into the microneedle forming recesses, and the filled material partially intrude into the microneedle tip part intrusion recess; and after expiration of a predetermined curing, the substrate is removed from the female mold, so that the microneedle array, having the microneedle tip part installed on the top of each of the plurality of the microneedle base parts of the substrate, is obtained.

Moreover, the microneedle array manufacturing method of a mode (15) is characterized in that, with reference to the microneedle array manufacturing method of the mode (13) or the mode (14), the microneedle base part is fitted into the microneedle forming recess under laminar flow, in the direction perpendicular to the laminar flow.

Moreover, the microneedle array manufacturing method of a mode (16) is characterized in that, with reference to the microneedle array manufacturing method of any of the mode (13) to the mode (15), the dimensions of the microneedle tip part are controlled with adjustment of fitting amount of the microneedle base part into the microneedle forming recess.

Moreover, the microneedle array manufacturing method of a mode (17) is characterized in that, with reference to the microneedle array manufacturing method of any of the mode (13) to the mode (16), the microneedle tip part intrusion recess formed in the microneedle base part is penetration hole or groove.

Moreover, the microneedle array manufacturing method of a mode (18) is characterized in that, with reference to the microneedle array manufacturing method of any of the mode (13) to the mode (17), the female mold is made of an elastomer material.

Moreover, the microneedle array manufacturing method of a mode (19) is characterized in that, with reference to the microneedle array manufacturing method of any of the mode (13) to the mode (18), a projection is provided on the edge of the microneedle forming recess of the female mold.

Moreover, the microneedle array manufacturing method of a mode (20) is characterized in that, with reference to the microneedle array manufacturing method of any of the mode (13) to the mode (19), passages are formed in the female mold and the substrate for communicating the microneedle forming recesses with the outside.

Effect of the Invention

As discussed above, the microneedle array of the mode (1) of the present invention is comprising: a substrate; a plurality of microneedle base parts protrusively formed on the substrate integrally; and a microneedle tip part installed on the top of each of the plurality of microneedle base parts, respectively, so as to constitute a microneedle, provided with in vivo solubility and biodegradability, and holding an objective substance, and is characterized in that: a microneedle tip part intrusion recess is formed in the microneedle base part; and the microneedle tip part partially intrudes into the microneedle tip part intrusion recess. Therefore, any unintended drop-off of the microneedle tip part is prevented, and further, with the reinforced the strength of the microneedle, any damage during puncturing is prevented and the sure puncturing can be performed, and consequently, it is possible to surely administrate a desired volume of the objective substance.

Moreover, according to the microneedle array of a mode (2), with reference to the microneedle array of the mode (1), the microneedle tip part intrusion recess is penetration hole or groove. Therefore, the above effect can be achieved more surely.

Moreover, according to the microneedle array of a mode (3), with reference to the microneedle array of the mode (1) or the mode (2), the plurality of microneedles is punctured into the skin and is then pulled out, so that the microneedle tip parts remain under the skin. Therefore, the substrate can be removed immediately after puncturing, and it is not necessary to stay the substrate on the skin surface, and consequently, the burden on a patient can be relieved.

Moreover, according to the microneedle array of a mode (4), with reference to the microneedle array of any of the mode (1) to the mode (3), the microneedle tip part is provided with a perpendicular part. Therefore, via the perpendicular part, a friction is generated between the microneedle tip part and the skin, whereby the microneedle tip part remains inside the skin more surely.

Moreover, according to the microneedle array of a mode (5), with reference to the microneedle array of the mode (4), an uneven part is formed in the perpendicular part of the microneedle tip part. Therefore, the microneedle tip part remains inside the skin still more surely.

Moreover, according to the microneedle array of a mode (6), with reference to the microneedle array of any of the mode (1) to the mode (5), the cross sections of the microneedle base part and the microneedle tip part are rectangle. Therefore, when the microneedles are punctured into the skin, the friction is generated against the skin, whereby the microneedle tip part remains inside the skin still more surely.

Moreover, according to the microneedle array of a mode (7), with reference to the microneedle array of any of the mode (1) to the mode (6), a protrusion is formed on the microneedle base part on the side of the microneedle tip part, and the microneedle tip part is installed on the microneedle base part so as to cover the protrusion. Therefore, as compared with the microneedle base part having a flat surface on the side of the microneedle tip part, the strength of the microneedle can be reinforced. Moreover, with the reinforced strength, the microneedles can be removed from the female mold easily.

Moreover, according to the microneedle array of a mode (8), with reference to the microneedle array of any of the mode (1) to the mode (7), the substrate and the microneedle base parts are made of resin. Therefore, the strength of the microneedle can be reinforced further. Moreover, because of resin, it is possible to manufacture by various forming methods such as injection molding or hot embossing, whereby the production cost can be reduced, and the mass production can be facilitated.

Moreover, according to the microneedle array of a mode (9), with reference to the microneedle array of the mode (8), the resin is a biocompatible resin. Therefore, it is possible to minimize any potential risk to the human body.

Moreover, according to the microneedle array of a mode (10), with reference to the microneedle array of the mode (8), the resin is a biodegradable resin. Therefore, it is possible to minimize any potential risk to the human body.

Moreover, according to the microneedle array of a mode (11), with reference to the microneedle array of the mode (8), the resin is an in vivo insoluble resin. Therefore, it is possible to minimize any potential risk to the human body, and also, to reinforce the strength of the microneedles.

Moreover, according the microneedle array of a mode (12), with reference to the microneedle array of any of the mode (1) to the mode (11), a barb is formed in the microneedle tip part. Therefore, the microneedle tip part remains inside the skin still more surely.

Moreover, a microneedle array manufacturing method of a mode (13) is characterized in that: a female mold provided with microneedle forming recesses is prepared, and also a substrate, having an integrally formed plurality of microneedle base parts each of which provided with a microneedle tip part intrusion recess formed therein, is prepared; the substrate is installed in the female mold so that the plurality of microneedle base parts is fitted into the microneedle forming recesses; a dissolved or melted material, constituting a microneedle tip part and containing an objective substance, is filled in the microneedle forming recess, so that the filled material partially intrude into the microneedle tip part intrusion recess; and after expiration of a predetermined curing, the substrate is removed from the female mold, so that the microneedle array, having the microneedle tip part installed on the top of each of the plurality of the microneedle base parts of the substrate, is obtained. Therefore, it is possible to manufacture the microneedle array easily, in which the material is partially intruding into the microneedle tip part intrusion recess. Moreover, at that time, it is possible to prevent any contamination of impurities from the outside.

Moreover, a microneedle array manufacturing method of a mode (14) is characterized in that: a female mold provided with microneedle forming recesses is prepared, and also a substrate, having an integrally formed plurality of microneedle base parts each of which provided with a microneedle tip part intrusion recess formed therein, is prepared; a dissolved or melted material, constituting a microneedle tip part and containing an objective substance, is filled in the microneedle forming recess; the substrate is installed in the female mold, so that, the plurality of microneedle base parts is fitted into the microneedle forming recesses, and the filled material partially intrude into the microneedle tip part intrusion recess; and after expiration of a predetermined curing, the substrate is removed from the female mold, so that the microneedle array, having the microneedle tip part installed on the top of each of the plurality of the microneedle base parts of the substrate, is obtained. Therefore, also in this mode, it is possible to manufacture the microneedle array easily, in which the material is partially intruding into the microneedle tip part intrusion recess. Moreover, at that time, even in the case that the dissolved or melted objective substance is in high viscosity, it is possible to fill in the microneedle forming recess easily, and moreover, the adjustment of the material volume is also easy.

Moreover, according to the microneedle array manufacturing method of a mode (15), with reference to the microneedle array manufacturing method of the mode (13) or the mode (14), the microneedle base part is fitted into the microneedle forming recess under laminar flow, in the direction perpendicular to the laminar flow. Therefore, by preventing any contamination of impurities from the outside, it is possible to manufacture the microneedles in an aseptic condition.

Moreover, according to the microneedle array manufacturing method of a mode (16), with reference to the microneedle array manufacturing method of any of the mode (13) to the mode (15), the dimensions of the microneedle tip part are controlled with adjustment of fitting amount of the microneedle base part into the microneedle forming recess. Therefore, the dimensions of the microneedle tip part, that is, the material, and consequently, the volume of the objective substance, can be adjusted easily.

Moreover, according to the microneedle array manufacturing method of a mode (17), with reference to the microneedle array manufacturing method of any of the mode (13) to the mode (16), the microneedle tip part intrusion recess formed in the microneedle base part is penetration hole or groove. Therefore, a solution constituting the microneedle tip part can be solidified effectively. Moreover, when the substrate is fitted into the female mold, or when the dissolved or melted material constituting the microneedle tip part is injected into the female mold, the penetration hole or the groove serves as an air vent, whereby the substrate can be fitted into the female mold easily, and the dissolved or melted material constituting the microneedle tip part can be injected into the female mold easily. Moreover, any excess dissolved or melted material constituting the microneedle tip part can be extracted into the penetration holes and grooves. Moreover, by using the penetration hole, it is also possible to inject the dissolved or melted material constituting the microneedle tip part, into the female mold.

Moreover, according to the microneedle array manufacturing method of a mode (18), with reference to the microneedle array manufacturing method of any of the mode (13) to the mode (17), the female mold is made of an elastomer material. Therefore, the part between the microneedle forming recess and the microneedle base part can be sealed, and accordingly, it is possible to prevent any leakage of solution constituting the microneedle tip part. Moreover, due to elastic force of the female mold, the finished microneedle array can be removed easily. Moreover, the female mold made of elastomer material contributes to the cost reduction and the mass productivity, by casting and injection molding.

Moreover, according to the microneedle array manufacturing method of a mode (19), with reference to the microneedle array manufacturing method of any of the mode (13) to the mode (18), a projection is provided on the edge of the microneedle forming recess of the female mold. Therefore, when the substrate is fitted into the female mold, even if there is any disposition gap between the microneedle base part of the substrate and the microneedle forming recess, the gap is eliminated by movement and deformation of the projection, and accordingly, every microneedle base part of the substrate can be inserted into every microneedle forming recess easily. Moreover, with the adjustment of the size of the projection, the insertion depth of the microneedle base part into the microneedle forming recess can be adjusted, whereby the size of the microneedle tip part of the manufactured microneedle array can be adjusted.

Moreover, according to the microneedle array manufacturing method of a mode (20), with reference to the microneedle array manufacturing method of any of the mode (13) to the mode (19), passages are formed in the female mold and the substrate for communicating the microneedle forming recesses with the outside. Therefore, via the passage, the volatile ingredient can be vaporized easily out of the objective substance, whereby the drying (curing) period can be shortened. Moreover, with the supply of dry air into the microneedle forming recess via the passage, it is also possible to facilitate the drying (curing).

BRIEF DESCRIPTION OF DRAWINGS

FIG. 7 Drawings showing the first embodiment of the present invention, namely: FIG. 7 (*a*) is a sectional view showing a state immediately before the substrate of the microneedle array is fitted into the female mold used for manufacturing of the microneedle array according to the first embodiment; FIG. 7 (*b*) is a sectional view showing a state that the substrate is fitted into the female mold; FIG. 7 (*c*) is a sectional view showing a state that materials of microneedle tip parts are filled in recesses of the female mold via penetration holes of the substrate; and FIG. 7 (*d*) is a sectional view showing a state that, after the elapse of a predetermined curing period, the finished microneedle array is removed from the female mold.

FIG. 8 Drawings showing the first embodiment of the present invention, in which: FIG. 8 (*a*) is a sectional view showing a state that the materials of the microneedle tip parts are filled in the recesses of the female mold used for manufacturing of the microneedle array according to the first embodiment; FIG. 8 (*b*) is a sectional view showing a state immediately before the substrate of the microneedle array is fitted into the female mold; FIG. 8 (*c*) is a sectional view showing a state that the substrate is fitted into the female mold; and FIG. 8 (*d*) is a sectional view showing a state that, after the elapse of a predetermined curing period, the finished microneedle array is removed from the female mold.

FIG. 9 Drawings showing the first embodiment of the present invention, in which: FIG. 9 (*a*) is a view showing a state that the microneedle array is punctured into the skin according to the first embodiment; FIG. 9 (b) is a view showing a state that an ejecting jig is inserted into the penetration holes of the microneedle array punctured into the skin; and FIG. 9 (c) is a view showing a state that, with the ejecting jig, the microneedle tip parts of the microneedle array remain under the skin, and only the substrate of the microneedle array is detached from the skin.

FIG. 26 Drawings showing Example 1 of the present invention, in which: FIG. 26 (a) is a view showing a part of the substrate with the description of dimension of each part; FIG. 26 (b) is a view showing a part of the female mold with the description of dimension of each part; FIG. 26 (c) is a view showing a part of a state that the substrate is set in the female mold; and FIG. 26 (d) is a view showing a part of the microneedle array with the description of dimension of each part.

FIG. 28 Drawings showing Example 2 of the present invention, in which: FIG. 28 (a) is a view showing a part of a substrate with the description of dimension of each part; FIG. 28 (b) is a view showing a part of a female mold with the description of dimension of each part; FIG. 28 (c) is a view showing a part of a state that the substrate is set in the female mold; and FIG. 28 (d) is a view showing a part of the microneedle array with the description of dimension of each part.

FIG. 31 Drawings showing Example 3 of the present invention, in which: FIG. 31 (a) is an expanded photograph showing a state before the microneedle array is punctured into a silicone rubber sheet; FIG. 31 (b) is an expanded photograph showing a state that the microneedle array is punctured into the silicone rubber; and FIG. 31 (c) is an expanded photograph showing a state that the microneedle array is removed from the silicone rubber and only a tip part remains in the silicone rubber.

FIG. 32 Drawings showing Example 3 of the present invention, in which: FIG. 32 (a) is a view showing a part of the substrate with the description of dimension of each part; FIG. 32 (b) is a view showing a part of the female mold with the description of dimension of each part; FIG. 32 (c) is a view showing a state that the substrate is set in the female mold; and FIG. 32 (d) is a view showing a part of the microneedle array with the description of dimension of each part.

MODE(S) FOR CARRYING OUT THE INVENTION

Firstly, a first embodiment of the present invention will be explained as below, with reference to FIG. 1 to FIG. 9.

Figure 1:
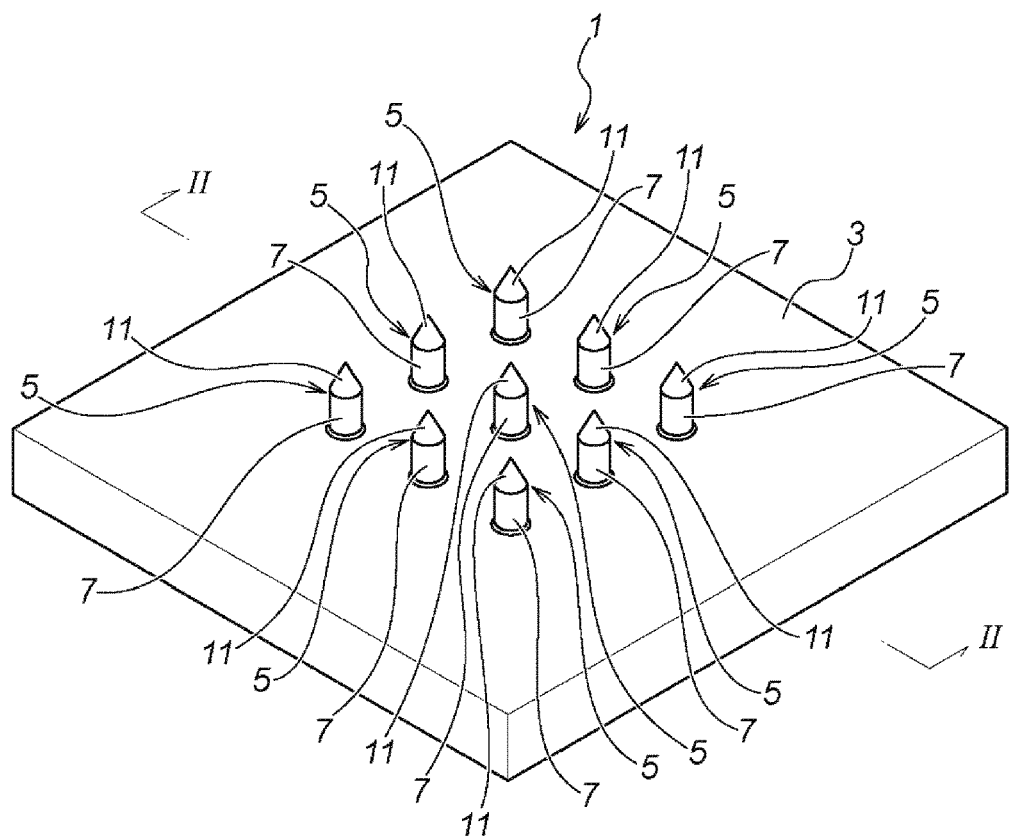
FIG. 1 A drawing showing a first embodiment of the present invention, namely, a perspective view of a microneedle array according to a first embodiment.
Figure 2:
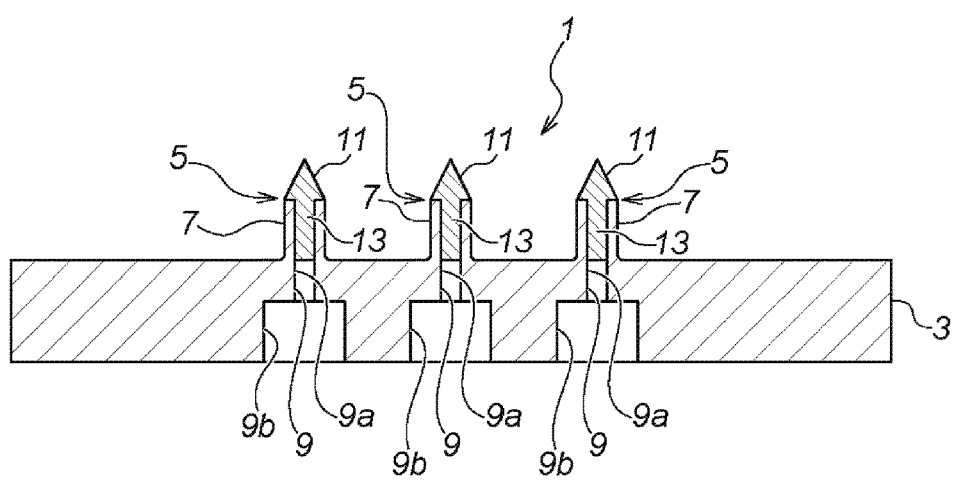
FIG. 2 A drawing showing the first embodiment of the present invention, namely, a sectional view as seen from the line II-II of FIG. 1, according to the first embodiment.

Firstly, a structure of a microneedle array 1 according to the first embodiment will be explained. As illustrated in FIG. 1 and FIG. 2, the microneedle array 1 is composed of a substrate 3 and a plurality of (in the present embodiment, nine) microneedles 5.

Note that, the term "microneedle array" in the present invention includes the "microneedle array 1," and moreover, other than the shape of the "microneedle array 1" shown in FIG. 1, also includes microneedle arrays according to a second to a ninth embodiments having various shapes and compositions, which will be explained afterwards.

Figure 3:
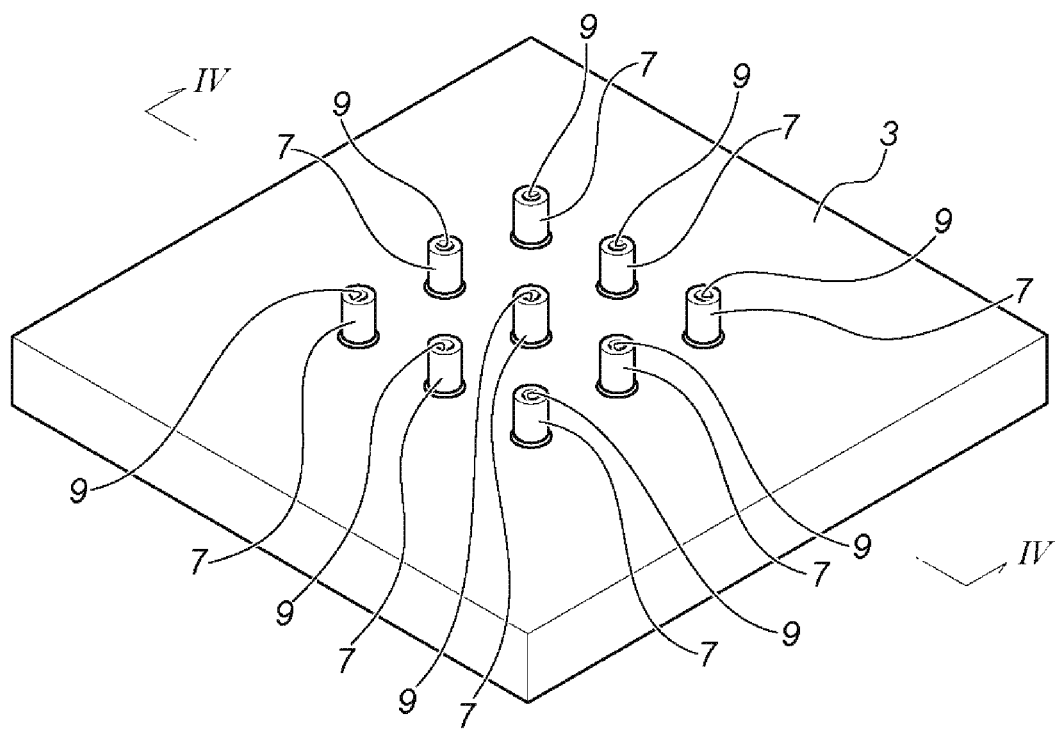
FIG. 3 A drawing showing the first embodiment of the present invention, namely, a perspective view of a substrate of the microneedle array according to the first embodiment.
Figure 4:
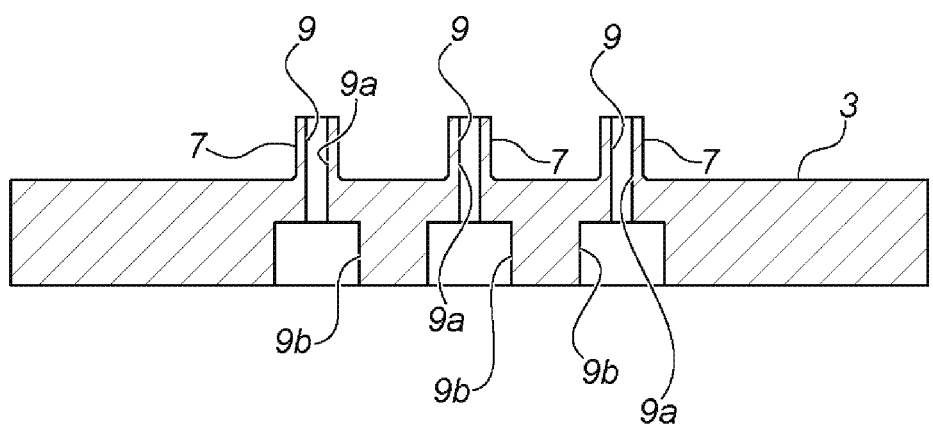
FIG. 4 A drawing showing the first embodiment of the present invention, namely, a sectional view as seen from the line IV-IV of FIG. 3, according to the first embodiment.

As illustrated in FIG. 3 and FIG. 4, the substrate 3 has a structure that a plurality of (in the present embodiment, nine) microneedle base parts 7 is protrusively formed upwardly in FIG. 4. Moreover, as illustrated in FIG. 4, in the substrate 3, a penetration hole 9, serving as a microneedle tip part intrusion recess, is formed separately in each of the microneedle base parts 7. Moreover, the penetration hole 9 has a smaller diameter part 9a on the side of the microneedle base part 7 (the upper part in FIG. 4), and also has a larger diameter part 9b on the side opposite to the microneedle base part 7 (the lower part in FIG. 4).

Moreover, as illustrated in FIG. 1 and FIG. 2, the microneedle 5 is composed of the microneedle base part 7 as already described, and a microneedle tip part 11 installed on the upper end surface of the microneedle base part 7 (the surface of the upper end side in FIG. 2).

As illustrated in FIG. 2, the top end side (the upper side in FIG. 2) of the microneedle tip part 11 is substantially in a conical shape, and from the bottom surface of this part substantially in the conical shape, a projection 13 having a smaller diameter is protrusively formed toward the substrate 3. The microneedle tip part 11 is installed on the upper end surface of the microneedle base part 7 (on the surface of the upper side in FIG. 2), in a state that the projection 13 intrudes into the smaller diameter part 9a of the penetration hole 9 of the microneedle base part 7.

Moreover, the state that the projection 13 intrudes into the smaller diameter part 9a of the penetration hole 9 of the microneedle base part 7 is accomplished by a material 19 in a dissolved or melted state, which constitutes the microneedle tip part 11 and contains an objective substance, intruding into the penetration hole 9 in the manufacturing process of the microneedle array 1, which will be described in detail afterwards.

Note that, as already described in the beginning, the objective substance means a medical agent, etc. Moreover, the term "dissolve" means a state in which a material containing the objective substance is solved in another solvent, etc., and the term "melt" means a state in which the material itself containing the objective substance is solved without requiring any auxiliary solvent, etc.

Moreover, as already described, the microneedle base parts 7 are protrusively formed on the substrate 3, and provided integrally on the substrate 3.

Moreover, the microneedle tip part 11 is formed by solidifying the dissolved or melted material, which has been prepared by mixing an in vivo soluble substance or a biodegradable substance as a base, with the objective substance administrated by the microneedle array 1.

Moreover, the substrate 3 and the microneedle base parts 7 are made of resin, and in the case of the first embodiment, a resin selected from a biodegradable resin, a biocompatible resin and an in vivo insoluble resin, or a mixture of any of these resins, is used.

Moreover, by considering the safety to human, it is preferable that the substrate 3 and the microneedle base parts 7 are composed of a biodegradable resin such as polylactic acid, polyglycolic acid, or lactic acid-glycolic acid copolymer or polydioxanone, or a mixture of any of these resins, and more preferably, they may be composed of polyglycolic acid having an excellent strength. Moreover, in view of the strength and not being damaged easily, it may also be composed of an in vivo insoluble versatile resin such as polycarbonate, polyethylene terephthalate or polystyrene.

As an example of biocompatible resin, polypropylene, Teflon (registered trademark) or polyurethane, as a single substance or a mixture of any of these substances, may be used.

Moreover, as for the size of the microneedle base part 7, by considering the facile puncturing, the strength and the facile manufacturing of the microneedle, the diameter is about 50 to 800 μm, preferably about 100 to 500 μm, and more preferably about 100 to 300 μm. Moreover, as for the height of the base part 7, from the viewpoints of the strength and manufacturing, it is preferable to set that the aspect ratio (height/diameter) is not more than 5, preferably not more than 3, and more preferably not more than 2. Moreover, as for the number of the base parts 7, although this is determined appropriately corresponding to the volume of medical agent required for the microneedle array 1 in the final form, the number is about 5 to 1000, preferably 10 to 800, and more preferably 100 to 500, per 1 $cm^2$.

Moreover, as for the size of the substrate 3, it is advantageous for handling that, in the case of a rectangular shape, one side is 1 to 50 mm, preferably one side is 5 to 30 mm, and more preferably one side is about 10 to 20 mm, and in the case of a round shape, the preferable diameter is 1 to 50 mm, preferably 5 to 30 mm, and more preferably about 10 to 20 mm.

Moreover, from the viewpoints of the production cost and the mass productivity, it is preferable that the substrate 3 and the microneedle base parts 7 are manufactured by any of various forming methods, such as injection molding, hot embossing or nanoimprinting.

Moreover, the penetration holes 9 may be penetrated by laser processing or the like after forming the substrate 3 and the microneedle base parts 7, but preferably, they may be formed simultaneously with the forming of the substrate 3 and the microneedle base parts 7. In the case that the penetration holes 9 are formed simultaneously with forming of the substrate 3 and the microneedle base parts 7, an unillustrated mold, which is used for forming of the substrate 3 and the microneedle base parts 7, shall be provided with projections or the like in advance, at the positions corresponding to the penetration holes 9.

Moreover, as for a base of the material of the microneedle tip part 11, this may be a water-soluble ultraviolet curing resin or an in vivo soluble substance, or may be in vivo insoluble substance, or a mixture of any of them. Also, any other additives may be added. As examples of in vivo soluble substances, as for saccharides, chondroitin sulfate, hyaluronic acid, heparin, amylose, amylopectin, glycogen, cellulose, carboxymethyl cellulose, hydroxypropyl cellulose, hydroxypropylmethylcellulose phthalate, dextrin, cyclodextrin, dextran, dextran sulfate, alginic acid, agarose, chitosan, pectin, glucomannan, pullulan, sucrose, lactose, trehalose, maltose and the salt thereof may be applied. As for polymers, polyvinylpyrrolidone, polyvinyl alcohol, carboxyvinyl polymer, polyacrylic acid-series polymers, polyethylene oxide, and the salt thereof, or a mixture of any two or more thereof, may be applied. Preferably, chondroitin sulfate, hyaluronic acid, polyvinylpyrrolidone, and the salt thereof, or a mixture of any two or more thereof, is applied.

As examples of in vivo insoluble substances, ethyl cellulose, methylmethacrylate-methacrylate copolymer, methylacrylate-methacrylate copolymer, cellulose acetate phthalate, polylactic acid, polyglycolic acid, lactic acid-glycolic acid copolymer, and the salt thereof, or a mixture of any two or more thereof, may be applied. Preferably, polylactic acid, polyglycolic acid, lactic acid-glycolic acid copolymer, and the salt thereof, or a mixture of any two or more thereof, may be applied.

When a water-soluble ultraviolet curing resin is used, since the excitation of polymerization is performed by ultraviolet irradiation after filling molecules having polymerization sites such a vinyl group, in particular, vinylpyrrolidone, styrene, styrenesulfonic acid, acrylic acid, methacrylic acid, acrylamide, isopropyl acrylamide, ethyleneimine, allylamine, and the salt thereof, or a mixture of any two or more thereof, is used. Preferably, vinylpyrrolidone, acrylic acid, methacrylic acid, and the salt thereof, or a mixture of any two or more thereof, is used.

As for other additives, collagen, gelatin, serum albumin, polyglutamic acid, and the salt thereof, or a mixture of any two or more thereof, may be applied.

Moreover, the diameter of the microneedle 5 is approximately 50 to 800 µm, preferably about 100 to 500 µm, and more preferably 100 to 300 µm. The preferable length of the microneedle 5 (the length in the upward/downward direction of FIG. 2) is about 200 to 1000 µm, and more preferably 300 to 800 µm. From the viewpoint of the strength, the length of the microneedle tip part 11 is preferably not more than the half of the overall length.

Note that, for the sake of explanation, although the number of the microneedles 5 is explained as nine as a model example, in actual, a large number of microneedles 5 is provided. Namely, as already explained, for example, the number per 1 $cm^2$ is 5 to 1000, preferably about 10 to 800, and more preferably 100 to 500.

However, in the scope of the present invention, the case that the number of the microneedle 5 is only one, is included.

As for the shape of the microneedle array 1 according to the first embodiment, a rectangular shape or a round shape is appropriate, but any other shape may be applied as long as it accomplishes the object of the present invention.

As for the size of the microneedle array 1 according to the first embodiment, although this has been already explained as the size of the substrate 3, for example, it is advantageous for handling that, in the case of a rectangular shape, one side is 1 to 50 mm, preferably one side is 5 to 30 mm, and more preferably one side is about 10 to 20 mm, and in the case of a round shape, the diameter is 1 to 50 mm, preferably 5 to 30 mm, and more preferably about 10 to 20 mm.

Moreover, it is also possible to provide an adhesive layer for adhering to the skin, on the surface of the substrate 3 of the microneedle array 1. As for adhesives, acrylic adhesive, rubber adhesive, or silicone adhesive may be used, and among them, any adhesive substance applied to medical tapes, such as acrylic adhesive or silicone adhesive, is more preferable. Moreover, the thickness of the adhesive layer is, for example, 1 to 200 µm, preferably about 5 to 150 µm, and more preferably 10 to 100 µm.

Moreover, although repeated, the objective substances in the first embodiment include medical agents, and with any medical agent serving as the objective substance, the microneedle array 1 in the first embodiment can be applied to the disease treatment and prevention of mammals (for example, humans, monkeys, sheep, horses, dogs, cats, rabbits, rats, mice, etc.) by using the medical agent.

As a using method of the microneedle array 1, it is possible to apply to any part on the skin of the mammals, and it is also possible to use on an uneven surface part.

The administration volume of the objective substance by the microneedle array 1 varies depending on the seriousness of symptom, the age, gender and weight of the administration subject, the administration period and intervals, and the type of active ingredients, and it is possible to select from the range that the administration volume as the medical active ingredients reaches the effective dose. Moreover, it is also possible to administrate the objective substance by the microneedle array 1, once a day, or divisionally twice or three times a day.

The applicable medical agents include, as for hormones, luteinizing hormone-releasing hormone analog, insulin, faster-acting insulin analog, long-acting insulin analog, ultra-long-acting insulin analog, growth hormone, PEGylation human growth hormone analog, somatomedin C, natriuretic peptide, glucagon, follicle-stimulating hormone, GLP-1 analog, parathyroid hormone analog, and as for enzymes, t-PA, glucocerebrosidase, alpha-galactosidase A, alpha-L-iduronidase, acid alpha-glucosidase, iduronate-2-sulfatase, human N-acetylgalactosamine-4-sulfatase, urate oxidase, deoxyribonuclease, and as for blood coagulation/fibrinolysis-associated factors, blood coagulation factor VIII, blood coagulation factor VII, blood coagulation factor IX, thrombomodulin, and as for serum proteins, albumin, and as for interferons, interferon-alpha, interferon-beta, interferon-gamma, PEGylation interferon-alpha, and as for erythropoietins, erythropoietin, erythropoietin analog, PEGylation erythropoietin, and as for cytokines, G-CSF, G-CSF derivative, interleukin-2, bFGF, and as for antibodies, mouse anti-CD3 antibody, humanized anti-EGF receptor antibody, chimeric anti-CD20 antibody, humanized anti-RS virus antibody, chimeric anti-TNF-alpha antibody, chimeric anti-CD25 antibody, humanized anti-IL6 receptor antibody, calicheamicin binding humanized anti-CD33 antibody, humanized anti-VEGF antibody, MX-DTPA binding mouse anti-CD20 antibody, human anti-TNF-alpha antibody, chimeric anti-EGFR antibody, humanized anti-VEGF antibody fragment, humanized IgE antibody, human anti-complement-C5 antibody, human anti-EGFR antibody, human anti-IL12/IL23-p40 antibody, human anti-IL-1-beta antibody, human anti-RANKL antibody, humanized anti-CCR4 antibody, PEGylation humanized anti-TNF-alpha antibody Fab, and as for fusion proteins, soluble TNF receptor Fc fusion protein, CTLA4-modified Fc fusion protein, Fc-TPOR agonist peptide fusion protein, VEGFR-Fc fusion protein, and as for vaccines, tetanus toxoid, diphtheria toxoid, pertussis vaccine, inactivated polio vaccine, live polio vaccine, diphtheria-tetanus combined toxoid, pertussis diphtheria tetanus mixed vaccine, *Haemophilus influenzae* b (Hib) vaccine, hepatitis B vaccine, hepatitis A vaccine, influenza hemagglutinin vaccine, rabies vaccine, Japanese encephalitis vaccine, Weil's disease autumnalis combined vaccine, pneumococcus vaccine, human papilloma virus vaccine, mumps vaccine, varicella vaccine, rubella vaccine, measles vaccine, rotavirus vaccine, norovirus vaccine, RSV vaccine, BCG vaccine. Further, any substances having an effect of assisting activation of the medical agents or an effect of immune system adjustment, are also included in the medical agents of the present invention, and for example, any adjuvants commonly used for manufacturing of vaccine formulations can be used. As for adjuvants, hardly water-soluble adjuvant, hydrophilic gel adjuvant or water-soluble adjuvant can be used. As for hardly water-soluble adjuvants, for example, retinoid such as retinoic acid, imiquimod, and imidazoquinolines such as Resquimod (R-848), 4-amino-α, α, 2-dimethyl-1H-imidazo[4,5-c]quinoline-1-ethanol (R-842 (made by 3M Pharmaceuticals, etc.); Journal of Leukocyte Biology (1995) 58: see 365-372), 4-amino-α, α, 2-trimethyl-1H-imidazo[4,5-c]quinoline-1-ethanol (S-27609 (made by 3M Pharmaceuticals, etc.); Journal of Leukocyte Biology (1995) 58: see 365-372), 4-amino-2-ethoxymethyl-α,α-dimethyl- 1H-imidazo[4,5-c]quinoline-1-ethanol (S-28463 (made by 3M Pharmaceuticals, etc.); Antivirul Research (1995) 28: see 253-264), and Loxoribine, Bropirimine, oleic acid, liquid paraffin, and Freund's adjuvant are included. As for hydrophilic gel adjuvants, for example, aluminum hydroxide and aluminum phosphate are included. As for water-soluble adjuvants, for example, alpha-defensin, beta-defensin, cathelicidin, sodium alginate, poly[di(carboxylatophenoxy)phosphazene], Quil A, polyethylene imine are included. The preferable adjuvants are hydrophilic gel adjuvants and water-soluble adjuvants. As for hydrophilic gel adjuvants, aluminum hydroxide and aluminum phosphate are included.

Moreover, among the microneedle arrays 1 of those as described above, it is particularly useful when the objective substance is a vaccine, and in this case, a vaccine antigen of a volume required for the disease treatment and prevention can be contained in the microneedle tip parts 11.

The target disease in the case that the objective substance is a vaccine, and the required volume therefor are described, for example in Japan, in "Biological Products Standards," published by Ministry of Health, Labor and Welfare, and in countries outside Japan, any equivalent official compendia of these countries. The volume of administrated medical agent cannot be defined unambiguously, because of the factors such as the object of vaccination (first vaccination or additional vaccination), whether or not the mixed vaccine, the age of vaccinated patient, the manufacturer, the virus strain, or the type, and therefore the volumes of medical agents used commonly will be described below as the examples, but the application of these medical agents to the present invention is not limited to these volumes.

For example, the volumes of the above medical agents are described as follows: (1) Tetanus: 2.5-5 Lf; (2) Diphtheria: 15-25 Lf; (3) Pertussis: 4 units or more; (4) Polio: Type 1: 1.5 DU, Type II: 50 DU, Type III: 50 DU; (5) Haemophilus influenzae b (Hib): 10 µg as polysaccharide; (6) Hepatitis B: 5-10 µg; (7) Hepatitis A: 0.5 µg; (8) Influenza hemagglutinin: 30 µg or more for each strain; (9) Rabies: 107 LD 50 or more; (10) Japanese encephalitis: equivalent to or more than reference preparation; (11) Weil's disease and autumnalis: 3 units or more; (12) Pneumococcus: 1-25 µg for each type as polysaccharide; (13) Human papilloma virus: 20-40 µg for each type; (14) Mumps: 5000 CCID 50 or more; (15) Varicella: 1000 PFU or more; (16) Rubella: 1000 PFU or more; (17) Measles: 5000 CCID 50 or more; (18) Rotavirus: 106 CCID 50 or more; (19) Norovirus: 5-150 µg; (20) RSV: 5-60 µg; (21) BCG: 12 µg.

The microneedle array 1 according to the first embodiment is useful for the disease treatment and prevention by the above medical agents, and also the low-toxic and safe medical formulation.

Moreover, the microneedle array 1 as described above may be used in combination with other medical formulations, such as oral administrating formulations or injection agents.

Figure 5:
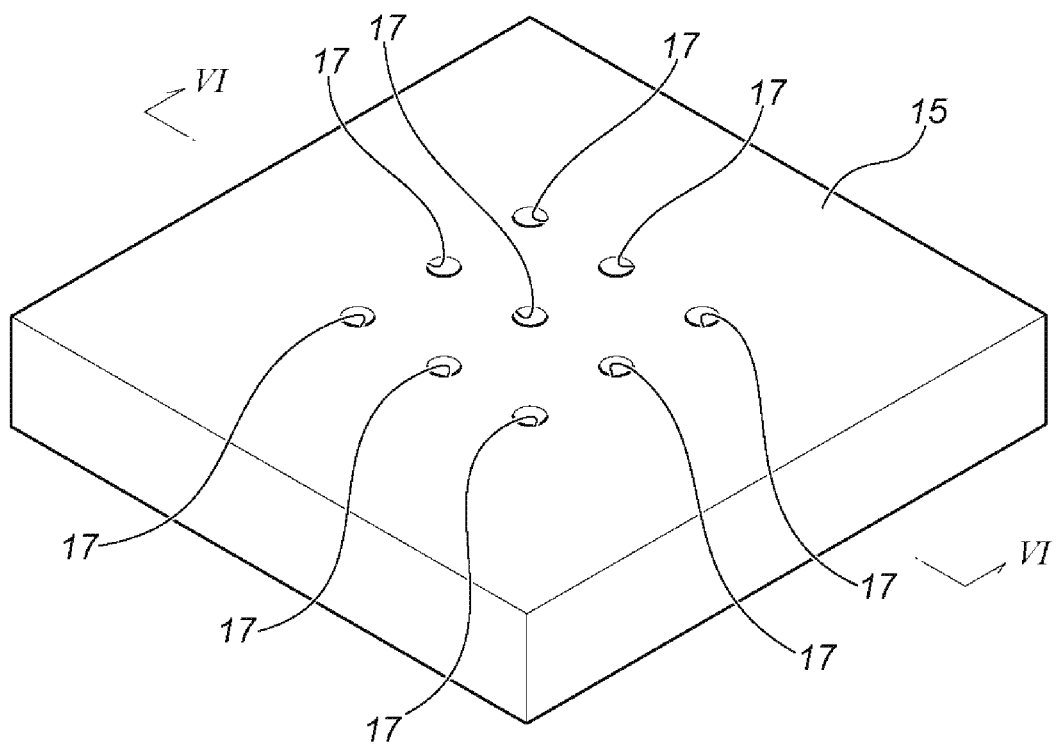
FIG. 5 A drawing showing the first embodiment of the present invention, namely, a perspective view of a female mold used for manufacturing of the microneedle array according to the first embodiment.
Figure 6:
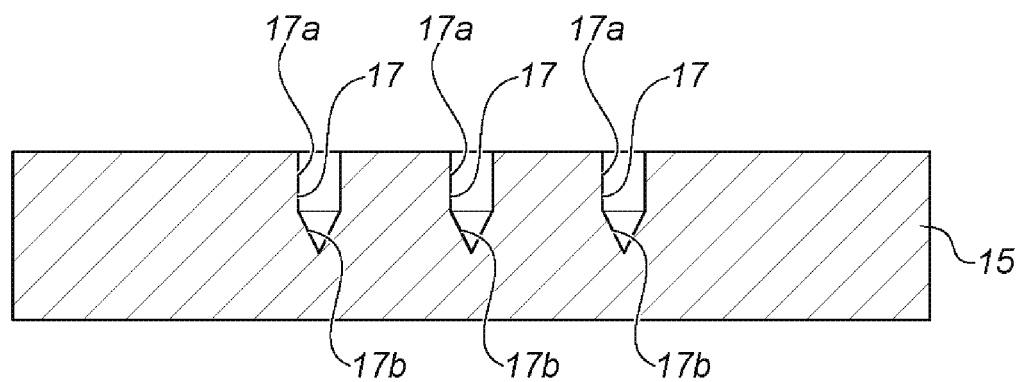
FIG. 6 A drawing showing the first embodiment of the present invention, namely, a sectional view as seen from the line VI-VI of FIG. 5, according to the first embodiment.

The microneedle array 1 according to the first embodiment is manufactured as below:

A female mold 15 as illustrated in FIG. 5 and FIG. 6 is used for manufacturing of the microneedle array 1. The female mold 15 has a plurality of microneedle forming recesses 17 formed therein. As illustrated in FIG. 6, the shape of the microneedle forming recess 17 corresponds to the shape of the microneedle 5 as described above, and is composed of a cylindrical recess section 17a and a reverse-conical recess section 17b.

Moreover, in the first embodiment, the female mold 15 is preferably made of elastomer from the viewpoint of elasticity, and more preferably, made of thermoplastic elastomer, silicone rubber or polyurethane rubber from the viewpoint of efficient molding. Moreover, the Shore hardness of the female mold 15 is preferably about A5 to A70, and more preferably, is A20 to A50.

The diameter of the microneedle forming recess 17 of the female mold 15 is 50 to 800 µm, preferably about 100 to 500 µm, and more preferably 100 to 300 µm. The depth at the longest point of the microneedle forming recess 17 is 300 to 1200 µm, preferably about 500 to 1000 µm, and more preferably 400 to 800 µm. The number of microneedle forming recesses 17 is 5 to 1000, preferably about 10 to 800, and more preferably 100 to 500 per 1 $cm^2$. The thickness of the female mold 15 is 0.3 to 10 mm, preferably about 0.5 to 5 mm, and more preferably 0.5 to 2 mm. The dimension, namely the size of each side or the diameter, of the female mold 15 is 5 to 50 mm, preferably 5 to 30 mm, and more preferably 10 to 20 mm.

Moreover, from the viewpoints of production cost and mass productivity, it is preferable that the female mold 15 is manufactured by injection molding or casting.

Moreover, from the viewpoint of workability when the substrate 3 is fitted into the female mold 15, the female mold 15 may be made of any transparent material.

Moreover, the dimension of the microneedle forming recess 17 (the diameter of the cylindrical recess section 17a) is set to be slightly smaller than the dimension (diameter) of the microneedle base part 7. More particularly, the diameter of the cylindrical recess section 17a of the microneedle forming recess 17 is set to be smaller than the diameter of the microneedle base part 7, by about 1 to 100 µm, preferably about 5 to 80 µm, and more preferably about 10 to 50 µm. Accordingly, when the substrate 3 is fitted into the female mold 15, no gap will emerge between the microneedle base part 7 and the microneedle forming recess 17, and therefore, any unintended leakage or unintended drop-off of the substrate 3 from the female mold 15 can be prevented.

Note that, however, the case that the dimensions coincide with each other is also included in the present invention.

The manufacturing of the microneedle array 1 according to the first embodiment is performed in the following process:

First, as illustrated in FIG. 7 (a), the female mold 15, and the substrate 3 as described above, are prepared.

Next, as illustrated in FIG. 7 (b), for example under the laminar flow, the microneedle base parts 7 of the substrate 3 are inserted in the microneedle forming recesses 17 of the female mold 15, and thereby, perpendicular to the laminar flow, the substrate 3 is fitted into the female mold 15.

Next, as illustrated in FIG. 7 (c), the materials 19 constituting the microneedle tip parts 11 are injected, via the penetration holes 9 of the substrate 3, into the microneedle forming recesses 17 of the female mold 15. As for the material 19, the objective substance is mixed to be dissolved or melted, in a resin selected from biodegradable resin, biocompatible resin, in vivo insoluble resin, ultraviolet curing resin and in vivo soluble resin as the base as described above, or the mixture thereof. At that time, the injected material 19 partially remains in the penetration hole 9 of the substrate 3. The injection of the material 19 into the microneedle forming recess 17 is performed, for example, by dispenser, ink-jet, potting, dispensing, syringe, etc. Moreover, because of the air in the microneedle forming recess 17, if the injection of the material 19 is difficult, it is possible to inject in a vacuum, or to provide small grooves, etc., for discharging the air in any part of the microneedle base part 7 or the female mold 15.

After the elapse of a predetermined curing period, the material 19 is solidified and becomes the microneedle tip part 11, whereby the microneedle array 1 provided with the plurality of microneedles 5 is constituted.

Thereafter, as illustrated in FIG. 7 (d), the finished microneedle array 1 is removed from the female mold 15. The removal of the microneedle array 1 from the female mold 15 is performed, immediately after completion of the microneedle array 1, or immediately before using of the microneedle array 1.

Moreover, the female mold 15 after removing the microneedle array 1 can be used again, but from the viewpoint of sanitation, etc., it is preferable to be a disposable type. Especially, when the microneedle array 1 is removed immediately before using, the female mold 15 is inevitably the disposable type.

Moreover, anther manufacturing method of the microneedle array 1 is explained with reference to FIG. 8.

Figures 8A, 8B, 8C, 8D:
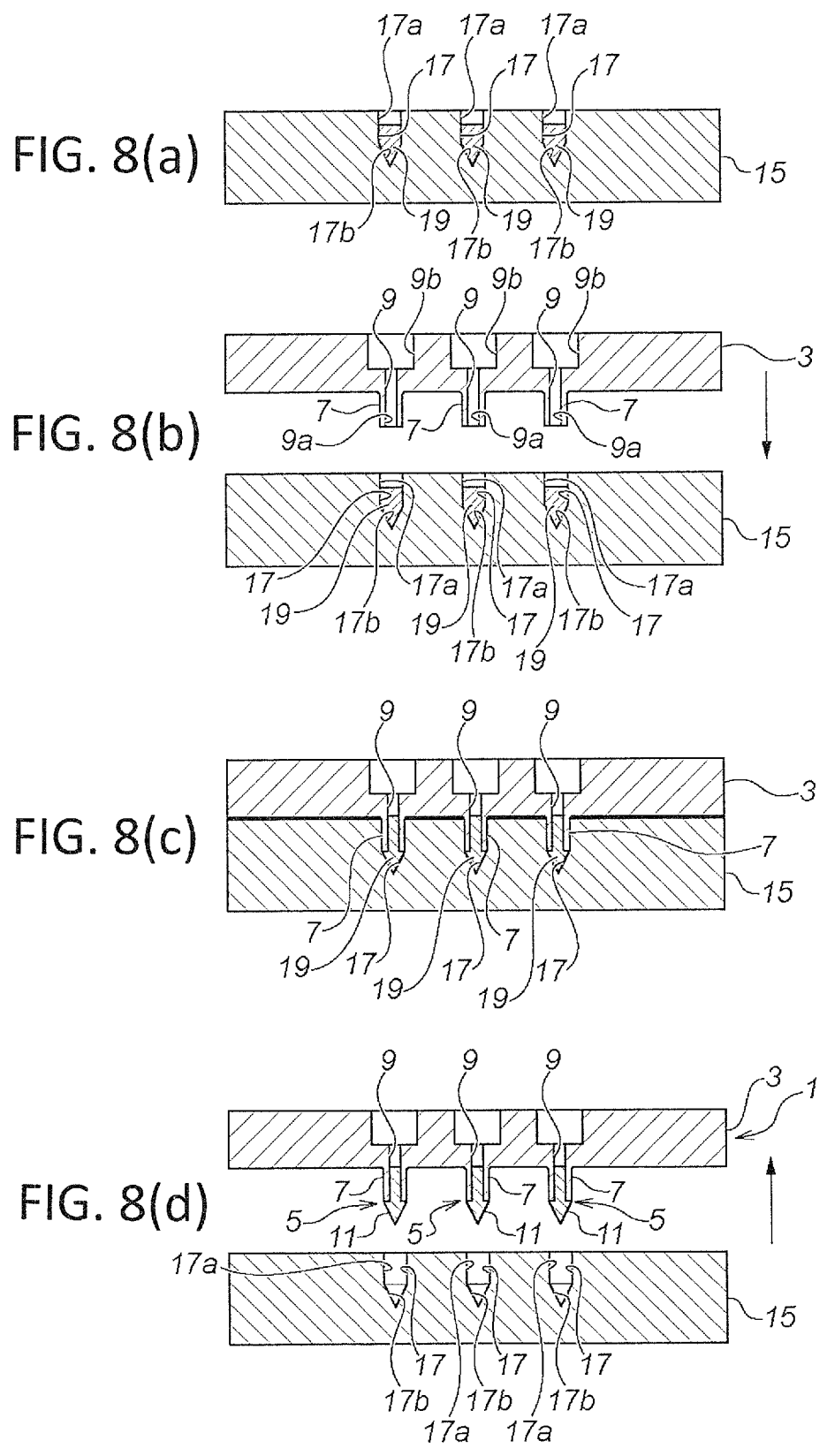

First, as illustrated in FIG. 8 (a), the material 19 has been injected in advance, into the microneedle forming recess 17 of the female mold 15. The injection of the material 19 into the microneedle forming recess 17 is performed, for example, by dispenser, ink-jet, spraying, potting, dispensing, syringe, printing, squeegee, etc.

Next, as illustrated in FIG. 8 (b) and FIG. 8 (c), under the laminar flow, and perpendicular to the laminar flow, the microneedle base parts 7 of the substrate 3 are inserted in the microneedle forming recesses 17 of the female mold 15, whereby the substrate 3 is fitted into the female mold 15. At that time, the material 19 partially infiltrates into the penetration hole 9 of the substrate 3.

After the elapse of a predetermined curing period, the material 19 is solidified and becomes the microneedle tip part 11, whereby the microneedle array 1 provided with the plurality of microneedles 5 is constituted.

Thereafter, as illustrated in FIG. 8 (d), the finished microneedle array 1 is removed from the female mold 15.

Figure 9A:
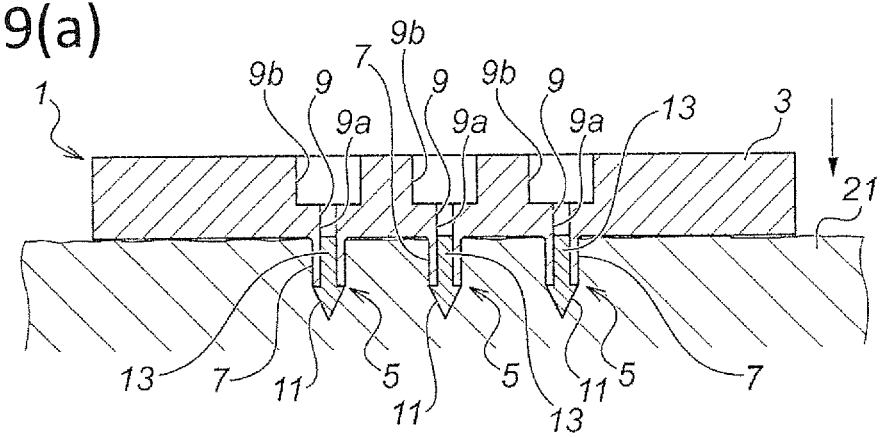
Figure 9B:
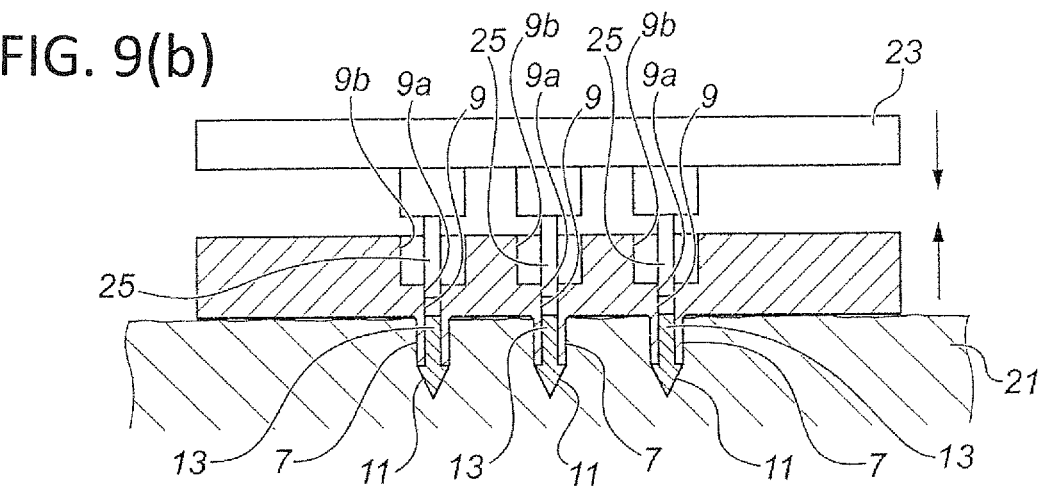
Figure 9C:
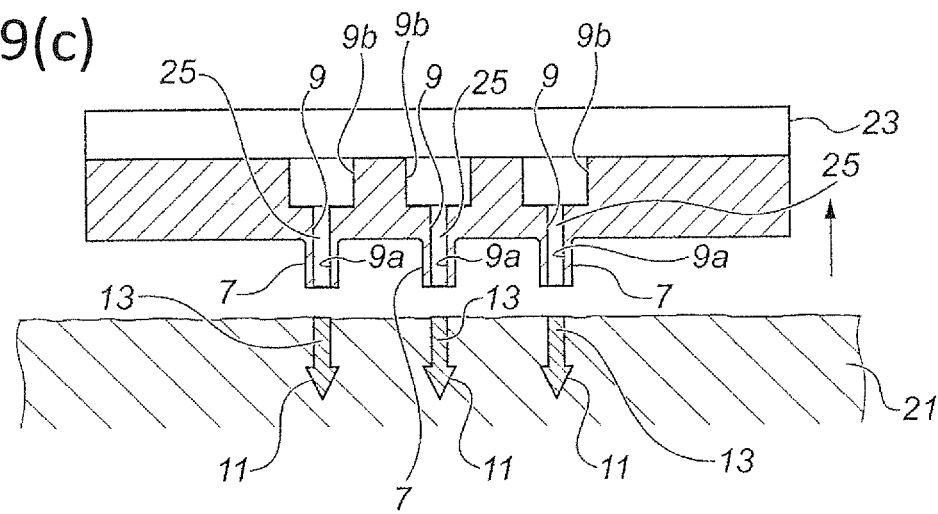

When the microneedle array 1 is used, as illustrated in FIG. 9 (a), each of the microneedles 5 is punctured into a skin 21 as the object of puncture. Thereafter, with passing of time, due to moisture and heat inside the skin 21, the microneedle tip parts 11 gradually melt and diffuse inside the skin 21.

Moreover, after puncturing, it is possible that the microneedle array 1 is left in a puncturing state until the microneedle tip parts 11 completely melt and diffuse inside the skin 21, but it is also possible that, immediately after puncturing, the substrate 3 of the microneedle array 1 is removed from the skin 21, so that only the microneedle tip parts 11 remain inside the skin 21. In this case, it is advantageous that, while the microneedle tip part 11 melt and diffuse inside the skin 21, the substrate 3 needs not to be adhering to the surface of the skin 21.

However, when the substrate 3 of the microneedle array 1 is merely removed from the skin 21, there is a concern that the microneedle tip parts 11 might be also removed from the skin 21 together with the substrate 3.

Therefore, according to the present embodiment, an ejecting jig 23 as illustrated in FIG. 9 (b) is used. Namely, as illustrated in FIG. 9 (b), the ejecting jig 23 is inserted in the respective penetration holes 9 of the substrate 3, so that the microneedle tip parts 11 are ejected while the substrate 3 is removed from the skin 21, whereby the microneedle tip parts 11 remain inside the skin 21.

As for the material of the ejecting jig 23, any versatile plastic or metal may be used, but if the disposable type is the prerequisite, from the viewpoint of production cost, any moldable plastic is preferable, and the manufacturing by injection molding, which is excellent for the mass productivity, is more preferable.

As illustrated in FIG. 9 (b) and FIG. 9 (c), the ejecting jig 23 has a plurality of projections 25 formed thereon, corresponding to the penetration holes 9 of the substrate 3. With the projections 25, the projections 13 of the microneedle tip parts 11 are biased, whereby the microneedle tip parts 11 are ejected out of the penetration holes 9.

Moreover, as an alternative, it is also possible that any ejecting jig such as the ejecting jig 23 is not used. For example, it is possible to eject the microneedle tip parts 11 out of the penetration holes 9 by air pressure, with the feeding of the compressed air from the penetration holes 9.

With the structure as described above, the function of the microneedle array 1 according to the first embodiment, namely, puncturing by the microneedle array 1, and melting and diffusion of the objective substance inside the skin, will be explained.

First, as illustrated in FIG. 9 (a), the microneedle array 1 is punctured into the skin 21. At that time, with passing of time, the microneedle tip parts 11 gradually by moisture and heat inside the skin 21, and diffuse inside the skin 21. Thus, the objective substance contained in the microneedle tip parts 11 is administrated inside the skin 21.

Moreover, after puncturing, there are two occasions, that the microneedle array 1 is left in a puncturing state, and that the substrate 3 is removed from the skin 21 immediately after puncturing.

When the microneedle array 1 is left in a puncturing state, in regard to the microneedle tip part 11, since the part in the penetration hole 9 is surrounded by the microneedle base part 7, as compared with the part on the side of the skin 21 of the microneedle tip part 11, the objective substance melts and diffuses slowly.

On the other hand, when the substrate 3 is removed from the skin 21, since the microneedle tip part 11, as well as the part 13 which has been intruding into the penetration hole 9, are covered directly by the skin 21, the objective substance melts and diffuses from the both parts. Therefore, as compared with the case that the microneedle array 1 is left in a puncturing state, the objective substance melts and diffuses more rapidly.

Moreover, when the substrate 3 is simply attempted to be removed from the skin 21, there is a possibility that the microneedle tip part 11 may be withdrawn from the skin 21 simultaneously. In such a case, as illustrated in FIG. 9 (b) and FIG. 9 (c), with the ejecting jig 23, the microneedle tip parts 11 are ejected from the penetration holes 9 of the substrate 3, so that only the microneedle tip parts 11 remain inside the skin 21.

As described above, the present embodiment has the following effects.

The microneedle 5 of the microneedle array 1 is composed of the microneedle base part 7 formed integrally with the substrate 3, and the microneedle tip part 11 installed on the microneedle base part 7 and containing the objective substance. Therefore, with the microneedle base part 7, the strength of the microneedle 5 is secured, whereby the sure puncturing and administration of the objective substance can be performed.

Moreover, since the diameter of the microneedle base part 7 is constant in the lengthwise direction (the upward/downward direction of FIG. 2), even in the case of deep puncturing inside the skin 21, the puncturing resistance will not increase, whereby the puncturing can be performed easily.

Moreover, when the substrate 3 and the microneedle base parts 7 are made of biodegradable or biocompatible material, by any possibility, if the microneedle base part 7 is broken inside the skin 21, the risk to the human body will be considerably small. Moreover, the facile handling can be secured even for aged persons or infants.

Moreover, when the substrate 3 and the microneedle base parts 7 are made of in vivo insoluble resin, the microneedle base part 7 will not melt in the body, thus the risk to the human body is considerably small.

Moreover, the substrate 3 is provided with the penetration holes 9 formed therein, serving as the microneedle tip part intrusion recesses, and in the manufacturing process of the microneedle array 1, the material 19 in a melted or dissolved state to constitute the microneedle tip part 11, infiltrates and remains in the penetration hole 9, whereby the projection 13 of the microneedle tip part 11 intrudes into the penetration hole 9. Accordingly, the microneedle tip part 11 is surely installed on the microneedle base part 7, and any unintended drop-off of the microneedle tip part 11 from the microneedle base part 7 is prevented, whereby the sure puncturing and administration of the objective substance can be performed.

Moreover, after puncturing, there are two occasions, that the microneedle array 1 is left in a puncturing state, and that the substrate 3 is removed from the skin 21 immediately after puncturing. When the microneedle array 1 is left in a puncturing state, in regard to the microneedle tip part 11, since the part in the penetration hole 9 is surrounded by the microneedle base part 7, as compared with the part on the side of the skin 21 of the microneedle tip part 11, the objective substance melts and diffuses slowly, and can be discharge gradually.

On the other hand, when the substrate 3 is removed from the skin 21, since the microneedle tip part 11, as well as the part 13 which has been intruding into the penetration hole 9, are covered directly by the skin 21, the objective substance melts and diffuses from the both parts. Therefore, as compared with the case that the microneedle array 1 is left in a puncturing state, the objective substance can melt and diffuse more rapidly.

Moreover, immediately after puncturing of the microneedle array 1 into the skin 21, at the time of removal of the substrate 3 from the skin 21, the projections 25 of the ejecting jig 23 are inserted in the penetration holes 9, so that the microneedle tip parts 11 are ejected, and thereby, only the microneedle tip parts 11 can surely remain inside the skin 21.

Moreover, since the microneedle array 1 is manufactured by using the female mold 15, which is provided with the microneedle forming recesses 17 formed therein corresponding to the shape of the microneedles 5, the microneedle array 1 having the microneedles 5 can be manufactured easily.

Moreover, the substrate 3 can be fitted into the female mold 15 under the laminar flow, and at that time, with the air supplied in the direction perpendicular to the fitting direction of the substrate 3 into the female mold 15, any intrusion of germs into the microneedle forming recesses 17 can be prevented, and as a result, the microneedle array 1 can be manufactured in an aseptic condition.

Moreover, when the microneedle array 1 is manufactured by fitting the substrate 3 into the female mold 15 after injecting material 19 into the microneedle forming recess 17, since the injection of the material 19 is performed in a state that the substrate 3 has not been fitted into the female mold 15, the injection of the material 19 into the microneedle forming recess 17 can be performed easily. Moreover, the injection volume of the material 19 can be adjusted easily.

Moreover, during manufacturing of the microneedle array 1 by using the female mold 15, when the substrate 3 is fitted into the female mold 15, the penetration holes 9 serve the function as the air vents, whereby the fitting of the substrate 3 into the female mold 15 can be performed easily. Moreover, any excess material 19 can be extracted into the penetration hole 9. In this case, since the microneedle tip part 11 partially intrudes into the penetration hole 9, the microneedle tip part 11 is engaged with the microneedle base part 7, and thereby any defect such as an unintended drop-off of the microneedle tip part 11 from the microneedle base part 7 can be prevented.

Moreover, during manufacturing of the microneedle array 1 by using the female mold 15, when the material 19 is solidified, with the penetration holes 9 of the substrate 3, the evaporation and vaporization of moisture or solvent in the material 19 can be performed effectively.

Moreover, the female mold 15 is made of elastomer, and the diameter of the microneedle forming recess 17 is set to be slightly smaller (smaller by about 10 to 50 μm) than the diameter of the microneedle base part 7. Therefore, during manufacturing of the microneedle array 1, the leakage of the material 19 can be prevented.

Note that, however, the case that the dimensions coincide with each other is also included in the present invention. Moreover, because of elastic force of the female mold 15, the finished microneedle array 1 can be removed easily.

In addition, because of elastic deformation of the female mold 15, even in the case that a slight gap exists between the microneedle base part 7 of the substrate 3 and the microneedle forming recess 17 of the female mold 15, the substrate 3 can surely be fitted into the female mold 15.

Now other embodiments of the present invention will be explained as below, in which, matters not described therein (for example, material, size, objective substance, functions, effects) are equivalent to those of the first embodiment.

Next, a second embodiment of the present invention will be explained with reference to FIG. 10.

Figure 10:
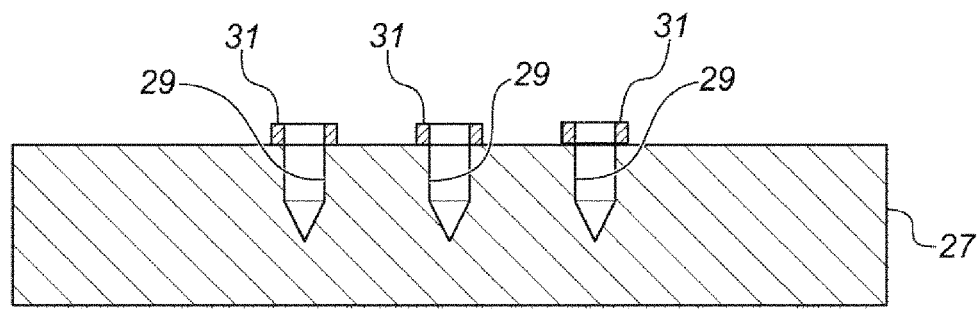
FIG. 10 A drawing showing a second embodiment of the present invention, namely, a sectional view of a female mold used for manufacturing of a microneedle array according to the second embodiment.

A microneedle array of the second embodiment has substantially the same structure as that of the microneedle array 1 of the first embodiment, but is manufactured by a female mold 27 as illustrated in FIG. 10.

Note that, the other structure is the same as that of the first embodiment, and for the sake of expedient explanation, reference signs such as the microneedle array 1, etc., will be used without change, in the explanation.

Likewise the case of the female mold 15 according to the first embodiment, the female mold 27 is provided with microneedle forming recesses 29 formed therein.

Moreover, as illustrated in FIG. 10, projections 31 are formed, respectively, at the upper end edge parts of the microneedle forming recesses 29 in FIG. 10. When the substrate 3 as described above is fitted into the female mold 27, the projection 31 is penetrated through by the microneedle base part 7, and becomes in contact with the substrate 3. Even in the case that any disposition gap occurs between the microneedle base part 7 of the substrate 3 and the microneedle forming recess 29 of the female mold 27, with the deformation of the projection 31, the disposition gap is eliminated, and thereby the microneedle base parts 7 of the substrate 3 can be inserted in the microneedle forming recesses 29 of the female mold 27 easily. Here, the projections 31 can be provided integrally when the female mold 27 is manufactured by injection molding, etc. In this case, parts corresponding to the projections 31 are provided in an unillustrated molding die. The height of the projection 31 can be determined depending on the required length of the microneedle 5 or the volume of the objective substance, but the height is 10 to 500 µm, preferably 30 to 300 µm, and more preferably 50 to 200 µm. The outer diameter of the projection 31 is 200 to 1000 µm, preferably 300 to 1000 µm, and more preferably 500 to 800 µm.

Moreover, with the adjustment of the length of the projection 31 in the upward/downward direction in FIG. 10, it is possible to adjust the insertion length of the microneedle base part 7 of the substrate 3 into the microneedle forming recess 29 of the female mold 27. Accordingly, the size of the microneedle tip part 11 of the manufactured microneedle array 1 can be adjusted easily. Moreover, it is also possible to set that the inner diameter of the projection 31 is slightly larger than the diameter of the microneedle forming recess 29. In this case, the upper part of the microneedle forming recess 29 (the upper side in FIG. 10) becomes wider, whereby the material 19 can be injected easily.

Note that, however, the case that the dimensions coincide with each other is also included in the present invention.

Moreover, in the state that the substrate 3 is fitted into the female mold 27, because of the projection 31, a space is formed around the projection 31. Therefore, the air as well as the volatile component of the objective substance can be discharged easily, whereby the curing period for drying of the material 19 can be shortened. Moreover, it is also possible to provide a slit as an air extractor in the projection 31 (the slit provided outwardly from the microneedle forming recess 29), and in this case, the curing period for drying of the material 19 can further be shortened. Here, it is preferable that the slit is formed integrally in a part of the surface of the projection 31, during molding of the projection 31. As for the size of the slit, since it is sufficient as long as the air is discharged, the width is 0.01 to 50 µm, preferably 0.05 to 20 µm, and more particularly, about 0.1 to 5 µm.

Figure 11:
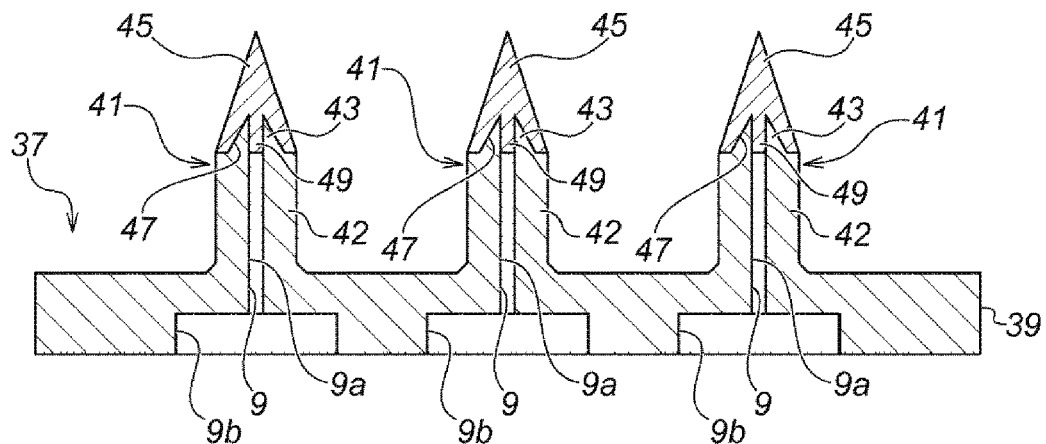
FIG. 11 A drawing showing a third embodiment of the present invention, namely, a sectional view of a microneedle array according to the third embodiment.

Next, a third embodiment of the present invention will be explained with reference to FIG. 11.

A microneedle array 37 according to the third embodiment is composed of a substrate 39, and a plurality of microneedles 41 disposed on the substrate 39. The structure of the substrate 39 is substantially the same as that of the substrate 3 of the microneedle array 1 according to the first embodiment, and is provided with microneedle base parts 42 protrusively formed thereon integrally. The structure of the microneedle base part 42 is substantially the same as that of the microneedle base part 7 in the first embodiment, and is substantially in a columnar shape, but a protrusion 43 substantially in a conical shape is protrusively formed on the upper end surface. The diameter of the bottom part of the protrusion 43 (the lower end part in FIG. 11) is set to be smaller than the diameter of the part substantially in the columnar shape of the microneedle base part 42. Moreover, a microneedle tip part 45 is installed on the upper end surface of the microneedle base part 42 so as to cover the protrusion 43. The microneedle tip part 45 has a recess 47, which corresponds to the shape of the protrusion 43, and a projection 49, which is projecting from the center of the recess 47 so as to intrude into the penetration hole 9 of the microneedle base part 42, formed therein. The length of the microneedle base part 42 may be substantially the same as the length of the microneedle base part 7 according to the first embodiment, but it is also possible to vary the length of the protrusion 43 corresponding to the length of the tip part 45. More in particular, the length of the protrusion 43 is 5 to 500 µm, preferably 10 to 300 µm, and more preferably 50 to 200 µm.

According to the microneedle array 37 of the third embodiment, it is possible to accomplish almost the same functions and effects as those of the microneedle array 1 of the first embodiment, and in addition, with the protrusions 43, the strength of the microneedle 41 can be reinforced.

Note that, with reference to the substrate 39, the same reference signs are allotted to the structural elements common to the substrate 3 of the microneedle array 1 according to the first embodiment, and the explanation thereof is not made here.

Figure 12:
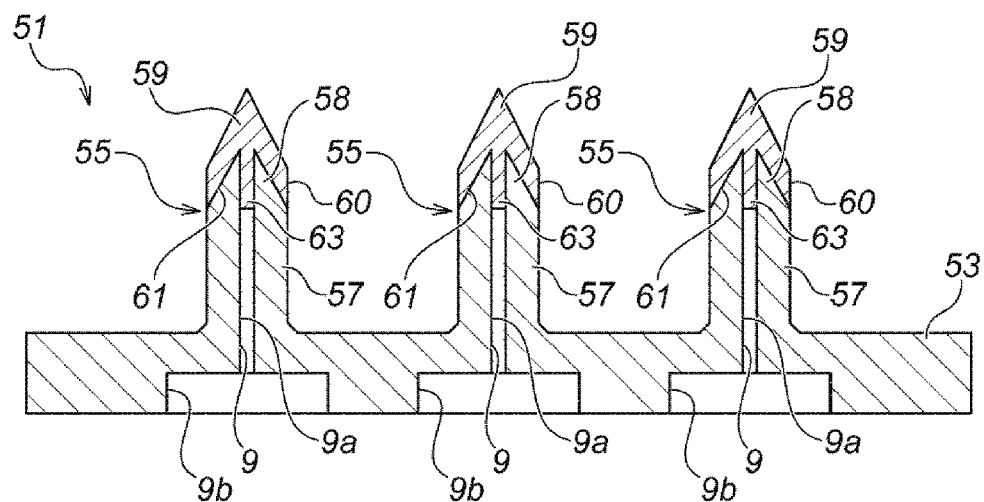
FIG. 12 A drawing showing a fourth embodiment of the present invention, namely, a sectional view of a microneedle array according to the fourth embodiment.

Next, a fourth embodiment of the present invention will be explained with reference to FIG. 12.

A microneedle array 51 according to the fourth embodiment is composed of a substrate 53, and a plurality of microneedles 55 disposed on the substrate 53. The structure of the substrate 53 is substantially the same as that of the substrate 3 of the microneedle array 1 according to the first embodiment, and is provided with microneedle base parts 57 protrusively formed thereon integrally. The lower section of the microneedle base part 57 in FIG. 12 is substantially in a columnar shape, but the upper section thereof in FIG. 12 is a protrusion 58 substantially in a conical shape. The diameter of the bottom part of the protrusion 58 (the lower end part of FIG. 12) is set to be equal to the diameter of the part substantially in the columnar shape of the microneedle base part 57. The length of the columnar-shape section is 100 to 1000 µm, preferably 200 to 800 µm, and more preferably about 300 to 500 µm.

Moreover, a microneedle tip part 59 is installed on the top end side of the microneedle base part 57. With reference to the microneedle tip part 59, the top end side thereof (the upper side in FIG. 12) substantially in a conical shape likewise the case of the microneedle tip part 11 of the microneedle array 1 according to the first embodiment, but the base end side thereof (the lower side in FIG. 12) is substantially in a columnar shape, and a perpendicular part 60 is formed on the outer peripheral surface. Moreover, the microneedle tip part 59 has a recess 61, which corresponds to the shape of the protrusion 58 of the microneedle base part 57, and a projection 63, which is projecting from the center of the recess 61 so as to intrude into the penetration hole 9 of the microneedle base part 57, formed therein.

According to the microneedle array 51 of the fourth embodiment, it is possible to accomplish almost the same functions and effects as those of the microneedle array 37 of the third embodiment. Moreover, since the microneedle tip part 59 is provided with the perpendicular part 60 substantially in a columnar shape on the lower side in FIG. 12, when the microneedle 55 is punctured inside the skin, with the perpendicular part 60, the friction is generated between the microneedle tip part 59 and the inside of the skin, whereby the microneedle tip part 59 surely remains inside the skin.

In this case, the ejection of the microneedle tip parts 59 by the ejecting jig 23 likewise the case of the first embodiment is not required, and by simply removing the substrate 53 after puncturing of the microneedle array 51, only the microneedle tip parts 59 may remain inside the skin. Of course, it is also possible to use the ejecting jig 23.

Note that, with reference to the substrate 53, the same reference signs are allotted to the structural elements common to the substrate 3 of the microneedle array 1 according to the first embodiment, and the explanation thereof is not made here.

Next, a fifth embodiment of the present invention will be explained with reference to FIG. 13.

Figure 13:
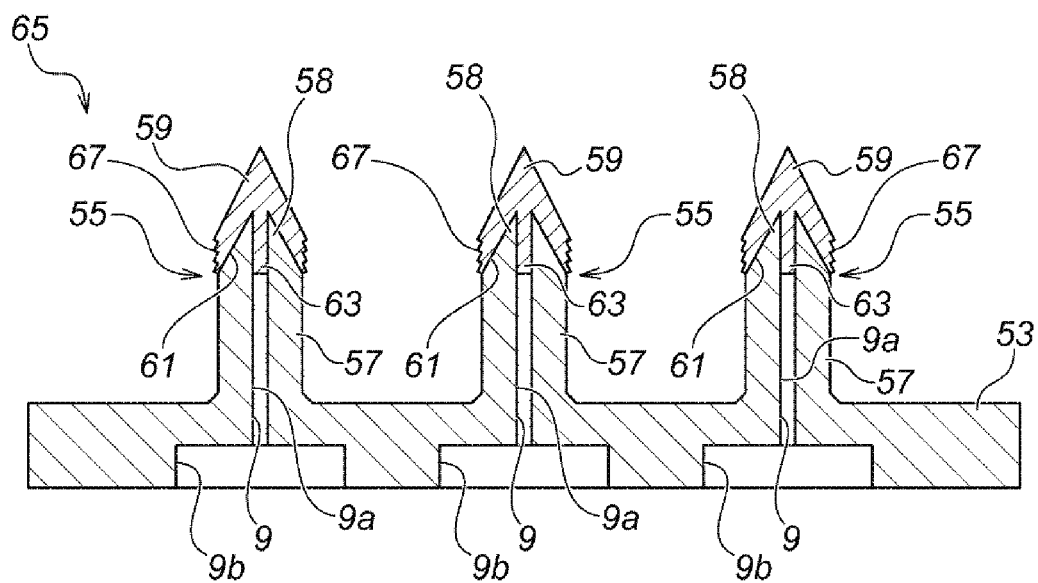
FIG. 13 A drawing showing a fifth embodiment of the present invention, namely, a sectional view of a microneedle array according to the fifth embodiment.

A microneedle array 65 of the fifth embodiment has substantially the same structure as that of the microneedle array 51 of the fourth embodiment, but is provided with an uneven part 67 formed on the outer peripheral surface of the part substantially in a columnar shape of the microneedle tip part 59, which is shown in the lower part of FIG. 13.

According to the microneedle array 65 of the fifth embodiment, it is possible to accomplish almost the same functions and effects as those of the microneedle array 51 of the fourth embodiment. Moreover, since the microneedle tip part 59 is provided with the uneven part 67 formed on the part substantially in a columnar shape on the lower side in FIG. 13, when the microneedle 55 is punctured inside the skin, with the uneven part 67, the friction is generated between the microneedle tip part 59 and the inside of the skin, whereby the microneedle tip part 59 remains inside the skin more surely.

Note that, with reference to the microneedle array 65, the same reference signs are allotted to the structural elements common to the microneedle array 51 according to the fourth embodiment, and the explanation thereof is not made here.

Figure 14:
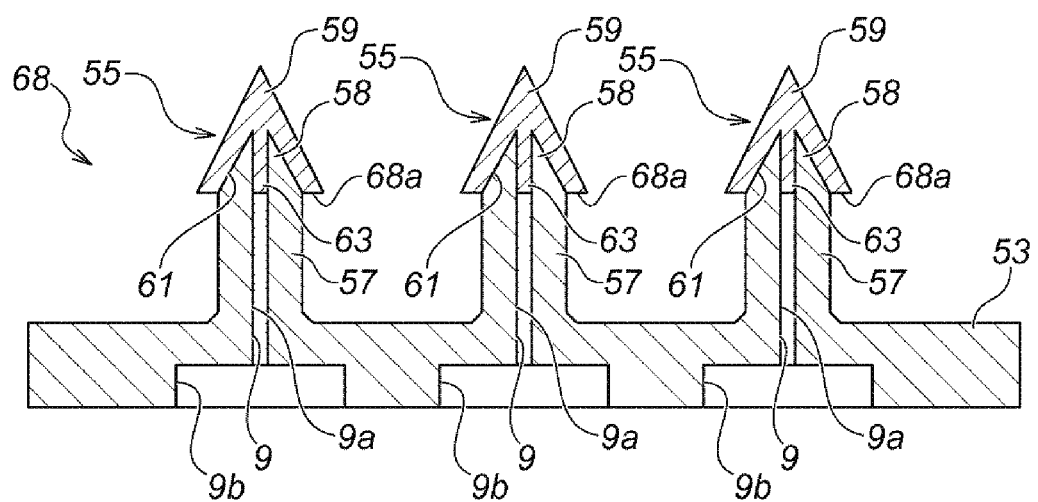
FIG. 14 A drawing showing a sixth embodiment of the present invention, namely, a sectional view of a microneedle array according to the sixth embodiment.

Next, a sixth embodiment of the present invention will be explained with reference to FIG. 14.

A microneedle array 68 of the sixth embodiment has substantially the same structure as that of the microneedle array 51 of the fourth embodiment, but the microneedle tip part 59 is substantially in a conical shape, of which diameter of the bottom surface (the surface on the lower side in FIG. 14) is set to be larger than the diameter of the microneedle base part 57. Accordingly, the bottom part of the microneedle tip part (the part on the lower side in FIG. 14) serves as a barb 68a.

According to the microneedle array 68 of the sixth embodiment, it is possible to accomplish almost the same functions and effects as those of the microneedle array 51 of the fourth embodiment. Moreover, since the microneedle tip part 59 is provided with the barb 68a formed therein, when the microneedle 55 is punctured inside the skin, the barb 68a of the microneedle tip part 59 engages with the skin, whereby the microneedle tip part 59 surely remains inside the skin.

Also in this case, the ejection of the microneedle tip parts 59 by the ejecting jig 23 likewise the case of the first embodiment is not required, and by simply removing the substrate 53 after puncturing of the microneedle array 68, only the tip parts may remain inside the skin. Of course, it is also possible to use the ejecting jig 23.

Moreover, as a problem during manufacturing of the microneedle array 68, it may be mentioned that the shape of the microneedle tip part 59 is in so-called "undercut shape." However, for example, by using the female mold made of elastomer, since the female mold is an elastic body, it is possible to remove the microneedle array 68 from the female mold easily, and the microneedle array 68 can be manufactured without any problem.

Note that, with reference to the microneedle array 68, the same reference signs are allotted to the structural elements common to the microneedle array 51 according to the fourth embodiment, and the explanation thereof is not made here.

Figure 15:
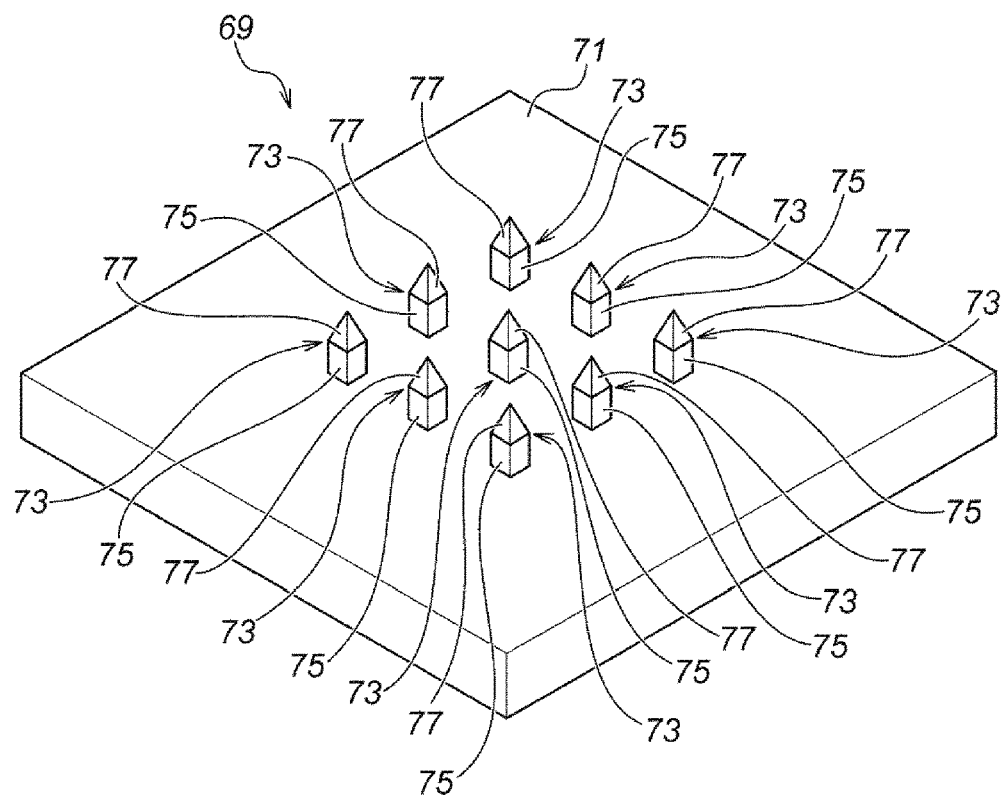
FIG. 15 A drawing showing a seventh embodiment of the present invention, namely, a perspective view of a microneedle array according to the seventh embodiment.

Next, a seventh embodiment of the present invention will be explained with reference to FIG. 15.

A microneedle array 69 according to the seventh embodiment is composed of a substrate 71, and a plurality of microneedles 73 disposed on the substrate 71. The structure of the substrate 71 is substantially the same as that of the substrate 3 of the microneedle array 1 according to the first embodiment, but is provided with microneedle base parts 75, each of which is substantially in a quadrangular prism shape, protrusively formed thereon integrally. Moreover, a microneedle tip part 77 substantially in a quadrangular pyramid shape, namely, of which cross-sectional shape is rectangle (quadrangle), is installed on the top end side of the microneedle base part 57.

According to the microneedle array 69 of the seventh embodiment, it is possible to accomplish almost the same functions and effects as those of the microneedle array 1 of the first embodiment. Moreover, since the cross-sectional shape of the microneedle tip part 77 is rectangle, when the microneedle 73 is punctured inside the skin, the friction is generated against the skin, whereby the microneedle tip part 77 surely remains inside the skin.

Note that, with reference to the substrate 71, the same reference signs are allotted to the structural elements common to the substrate 3 of the microneedle array 1 according to the first embodiment, and the explanation thereof is not made here.

Next, an eighth embodiment of the present invention will be explained with reference to FIG. 16 to FIG. 18.

Figure 16:
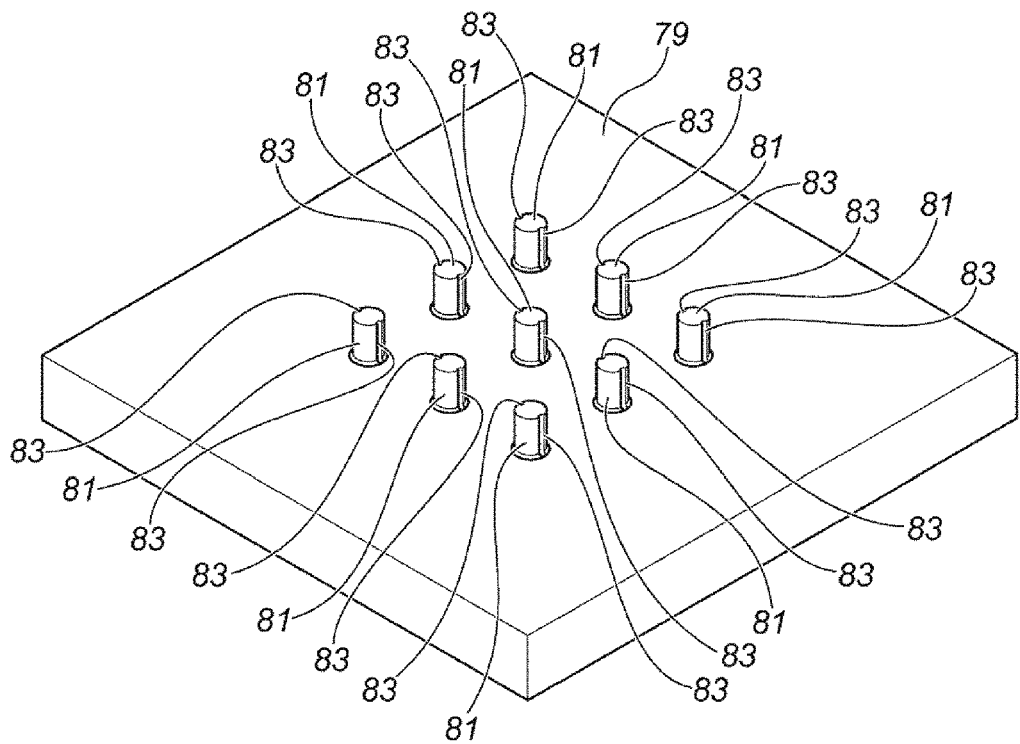
FIG. 16 A drawing showing an eighth embodiment of the present invention, namely, a perspective view of a substrate of a microneedle array according to the eighth embodiment.

A microneedle array according to the eighth embodiment uses a substrate 79 as illustrated in FIG. 16. The substrate 79 has a plurality of microneedle base parts 81 protrusively formed thereon. One or a plurality of (in the eighth embodiment, two) groove(s) 83, each of which is serving as a microneedle tip part intrusion recess, is formed in the outer periphery of the microneedle base part 81. Further, an unillustrated microneedle tip part is installed on the upper end side of the microneedle base part 81 (the upper side in FIG. 16). The unillustrated microneedle tip part is, for example, substantially in a conical shape, and is partially intruding into the grooves 83.

Figure 17:
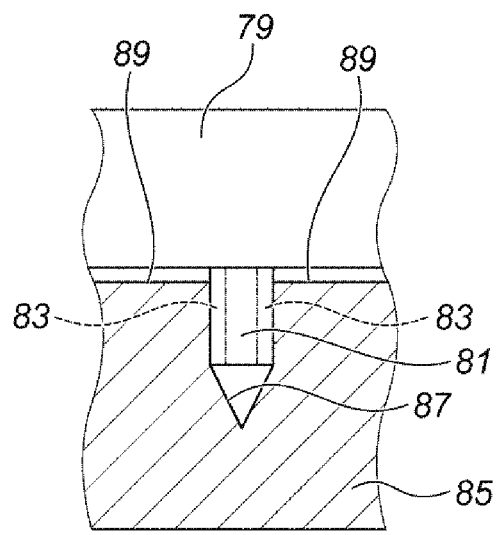
FIG. 17 A drawing showing the eighth embodiment of the present invention, namely, a partial expanded sectional view showing a state that the substrate is fitted into a female mold during manufacturing of the microneedle array according to the eighth embodiment.

A female mold 85 as illustrated in FIG. 17 is used for manufacturing of the microneedle array according to the eighth embodiment. The female mold 85 is provided with microneedle forming recesses 87, and grooves 89 communicating with the microneedle forming recesses 87, formed therein. The groove 89 elongates to a portion communicating with the outside when the substrate 79 is fitted into the female mold 85.

The microneedle array according to the eighth embodiment is manufactured in a method that, first, the material 19 is injected into the microneedle forming recess 87 of the female mold 85, and thereafter, the substrate 79 is fitted into the female mold 85. At that time, via the grooves 83 of the microneedle base parts 81 and the grooves 89 of the female mold 85, the air in the microneedle forming recesses 87 is extracted. Moreover, the material 19 partially intrudes into the grooves 83 of the microneedle base part 81, and as a result, with reference to the finished microneedle array, the unillustrated microneedle tip part partially intrudes into the grooves 83.

Figure 18:
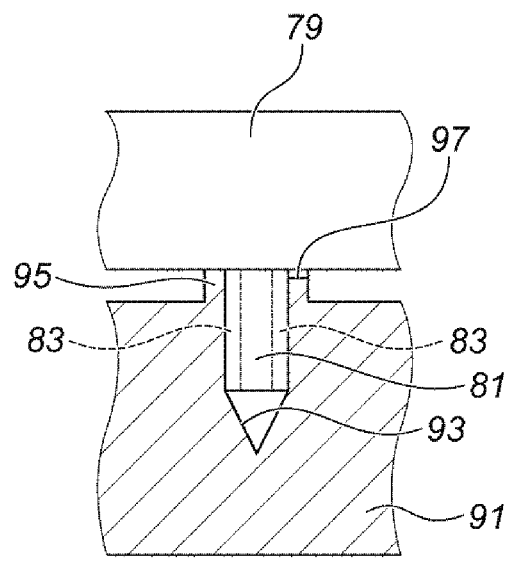
FIG. 18 A drawing showing the eighth embodiment of the present invention, namely, a partial expanded sectional view showing a state that the substrate is fitted into the female mold during manufacturing of the microneedle array according to the eighth embodiment.

Moreover, it is also possible to use a female mold 91 as illustrated in FIG. 18, for manufacturing of the microneedle array according to the eighth embodiment. The female mold 91 is provided with microneedle forming recesses 93 formed therein, and each of the microneedle forming recesses 93 is provided with a projection 95 formed on the upper side thereof, and a groove 97, formed in the upper end surface of the projection 95 (the end surface on the upper side in FIG. 18) and communicating with the microneedle forming recess 93. The projection 95 is substantially the same as the projection 31 of the female mold 27 in the second embodiment.

This microneedle array according to the eighth embodiment is manufactured in a method that, first, the material 19 is injected into the microneedle forming recess 93 of the female mold 91, and thereafter, the substrate 79 is fitted into the female mold 91. At that time, via the grooves 83 of the microneedle base parts 81 and the grooves 97 of the female mold 91, the air in the microneedle forming recesses 93 is extracted.

Also in this case, the material 19 partially intrudes into the grooves 83 of the microneedle base part 81, and as a result, with reference to the finished microneedle array, the unillustrated microneedle tip part partially intrudes into the grooves 83.

As for the diameter (in the case of providing in a arc-shape) or the width/depth (in the case of providing in a rectangular/square shape) of the grooves 83, 89 and 97, the preferable dimension is that the air passes smoothly, and that any unintended intrusion of the material 19 is prevented. In particular, the dimension is 0.01 to 100 μm, preferably 0.05 to 50 μm, and more preferably about 1 to 20 μm.

Moreover, in any of the above manufacturing methods, it is also possible that, via the grooves 89 or the grooves 97, and via the grooves 83, the dry air is supplied, so as to facilitate the volatilization and drying of moisture and solvent, etc., contained in the material of the microneedle tip parts.

According to the microneedle array of the eighth embodiment, it is possible to accomplish almost the same functions and effects as those of the microneedle array 1 of the first embodiment. Moreover, since the grooves 83 are formed in the outer periphery of the microneedle base part 81, during manufacturing of the microneedle array, when the substrate 79 is fitted into the female mold 85 or 91, the grooves 83 serve as the air vent, whereby the substrate 79 can be fitted into the female mold 85 or 91 easily. Moreover, via the grooves 83, the moisture and solvent, etc., contained in the material 19 of the microneedle tip part can be volatilized and dried, whereby the material of the microneedle tip part can be solidified effectively. Moreover, it is also possible to extract any excess material 19 into the grooves 83. Moreover, since there is no fine penetration hole provided in the substrate 79, the manufacturing of the microneedle array according to the present embodiment is relatively easy.

Moreover, the grooves 89 are formed in the female mold 85, and the grooves 97 are formed in the female mold 91. Therefore, during manufacturing as described above, it is possible to effectively perform the air extracting, as well as the volatilization and drying of moisture and solvent, etc., contained in the material 19 of the microneedle tip part.

Moreover, the projections 95 are formed on the female mold 91, whereby the space is provided around the projection 95. Therefore, during manufacturing as described above, it is possible to effectively perform the volatilization and drying of moisture and solvent, etc., contained in the material 19 of the microneedle tip part.

Figure 19:
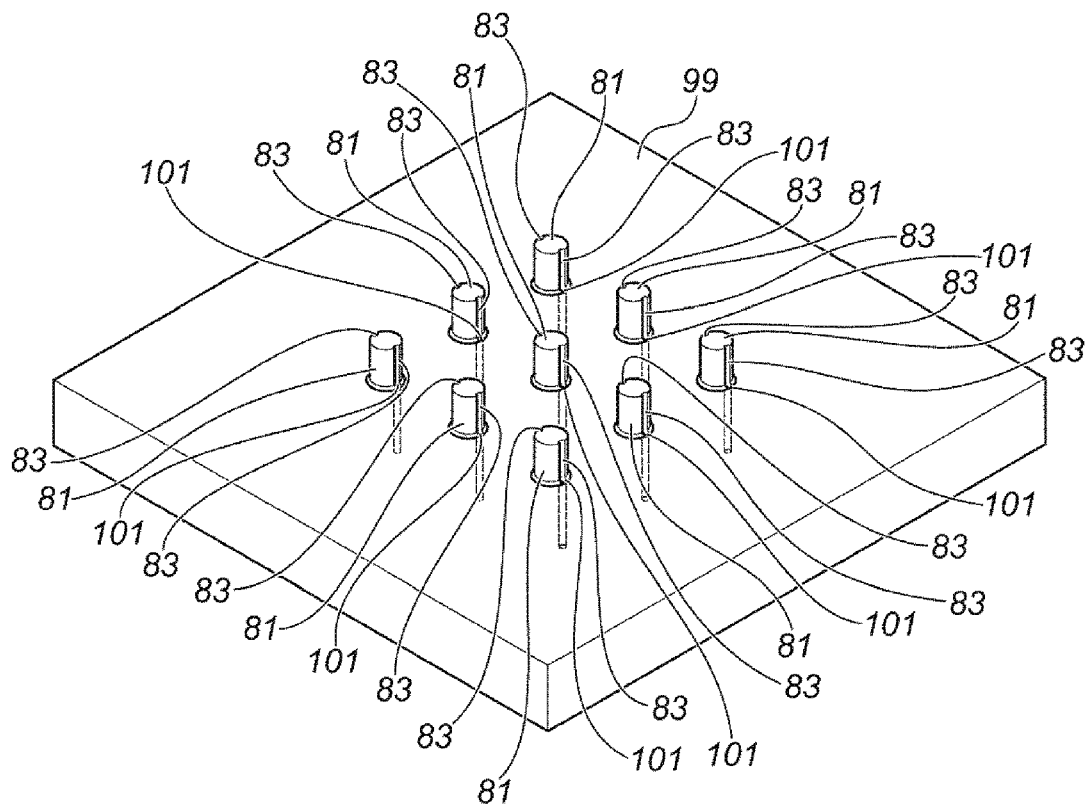
FIG. 19 A drawing showing a ninth embodiment of the present invention, namely, a perspective view of a substrate of a microneedle array according to the ninth embodiment.

Next, a ninth embodiment of the present invention will be explained with reference to FIG. 19 to FIG. 21. A substrate 99, which is used for manufacturing of a microneedle array according to the ninth embodiment, has substantially the same structure as that of the substrate 79 of the microneedle array in the eighth embodiment. However, as illustrated in FIG. 19, penetration holes 101, each of which communicates with the groove 83 serving as the microneedle tip part intrusion recess, and penetrates to the rear side of the substrate 99 (the lower side in FIG. 19), are also formed therein. At least one penetration hole 101 is formed in each of the microneedle base part 81.

Further, an unillustrated microneedle tip part is installed on the upper end side of the microneedle base part 81 (the upper side in FIG. 19). The unillustrated microneedle tip part is, for example, substantially in a conical shape, and partially intrudes into the grooves 83.

Note that, with reference to the substrate 99, the same reference signs are allotted to the structural elements common to the substrate 79 in the eighth embodiment, and the explanation thereof is not made here.

Figure 20:
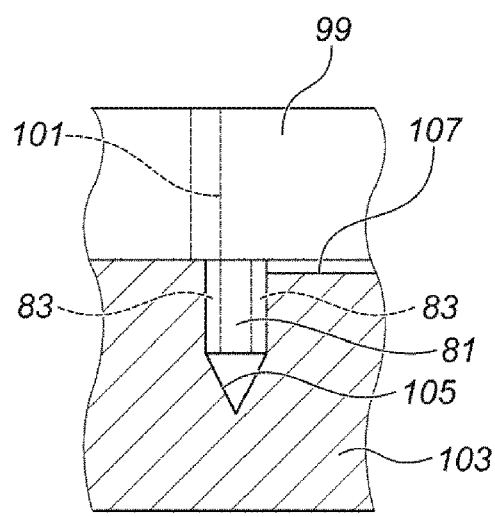
FIG. 20 A drawing showing the ninth embodiment of the present invention, namely, a partial expanded sectional view showing a state that the substrate is fitted into a female mold during manufacturing of the microneedle array according to the ninth embodiment.

A female mold 103 as illustrated in FIG. 20, which is substantially the same as the female mold 85 in the eighth embodiment as described above, is used for manufacturing of the microneedle array according to the ninth embodiment. The female mold 103 is provided with microneedle forming recesses 105, and grooves 107 communicating with the microneedle forming recesses 105, formed therein. The groove 107 is provided with an unillustrated opening communicating with the outside when the substrate 99 is fitted into the female mold 103.

For manufacturing of the microneedle array according to the ninth embodiment, there is a method that, first, the material 19 is injected into the microneedle forming recess 105 of the female mold 103, and thereafter, the substrate 99 is fitted into the female mold 103. In this method, via the grooves 83 of the microneedle base parts 81 and the grooves 107 of the female mold 103, and also via the penetration holes 101 of the substrate 99, the air in the microneedle forming recesses 105 is extracted.

There is also a method that, first, the substrate 99 is fitted into the female mold 103, and thereafter, via the penetration holes 101, the material 19 is injected into the microneedle forming recesses 105 of the female mold 103. In this method, via the grooves 83 and the grooves 107, the air in the microneedle forming recesses 105 is extracted.

Moreover, in any of the above manufacturing methods, it is also possible that, via the penetration holes 101, the grooves 107 and the grooves 83, the dry air is supplied, so as to facilitate the volatilization and drying of moisture and solvent, etc., contained in the material 19 of the microneedle tip parts.

Moreover, in any of the above manufacturing methods, likewise the case of the eighth embodiment, the material 19 partially intrudes into the grooves 83 of the microneedle base part 81, and the unillustrated microneedle tip part partially intrudes into the grooves 83.

Figure 21:
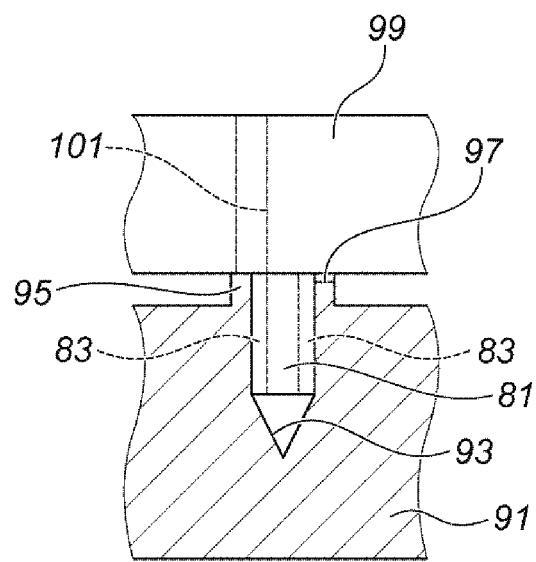
FIG. 21 A drawing showing the ninth embodiment of the present invention, namely, a partial expanded sectional view showing a state that the substrate is fitted into the female mold during manufacturing of the microneedle array according to the ninth embodiment.

Moreover, it is possible that, as illustrated in FIG. 21, the female mold 91 according to the eighth embodiment as described above, is used for manufacturing of the microneedle array according to the ninth embodiment.

For manufacturing of the microneedle array according to the ninth embodiment, there is a method that, first, an unillustrated material 19 is injected into the microneedle forming recess 93 of the female mold 91, and thereafter, the substrate 99 is fitted into the female mold 91. In this method, via the grooves 83 of the microneedle base parts 81 and the grooves 97 of the projections 95, and also via the penetration holes 101 of the substrate 99, the air in the microneedle forming recesses 93 is extracted.

Moreover, according to the microneedle array of the ninth embodiment, there is also a method that, first, the substrate 99 is fitted into the female mold 91, and thereafter, via the penetration holes 101 of the substrate 99, the material 19 is injected into the microneedle forming recesses 93. In this method, via the grooves 83 and the grooves 97, the air in the microneedle forming recesses 93 is extracted.

Moreover, in any of the above manufacturing methods, it is also possible that, via the penetration holes 101, the grooves 97 and the grooves 83, the dry air is supplied, so as to facilitate the volatilization and drying of moisture and solvent, etc., contained in the material 19 of the microneedle tip parts.

According to the microneedle array of the ninth embodiment, it is possible to accomplish almost the same functions and effects as those of the microneedle array of the eighth embodiment. Moreover, since the penetration holes 101 communicating with the grooves 83 of the microneedle base parts 81 are also formed therein, during manufacturing of the microneedle array, when the substrate 99 is fitted into the female mold, the grooves 83 and the penetration holes 101 serve as the air vent, whereby the substrate 99 can be fitted into the female mold 91 or 103 easily. Moreover, via the penetration hole 101, the material 19 can be injected into the microneedle forming recess 93.

Moreover, also via the penetration holes 101, the moisture and solvent, etc., contained in the material 19 of the microneedle tip part can be volatilized and dried, whereby the material 19 of the microneedle tip part can be solidified effectively. Moreover, it is also possible to extract any excess material 19, not only into the grooves 83, but also into the penetration hole 101.

Note that, the present invention is not limited to the first to the ninth embodiment as described above, and it is also possible to combine any of these embodiments.

For example, in the sixth embodiment, the barb 68*a* is formed on the microneedle tip part 59. In addition, it is possible to form a perpendicular part likewise the fourth embodiment in the microneedle tip part 59. Namely, with reference to the shape of the microneedle tip part 59, a part substantially in a cylindrical shape is added to the lower side of the barb 68*a* in the lower side of FIG. 14, and the outer peripheral surface of the part substantially in the cylindrical shape serves as the perpendicular part. In this case, with the addition of the perpendicular part, it is further facilitated that, only the microneedle tip part 59 remains inside the skin. Moreover, since the part substantially in the cylindrical shape is added thereto, it is possible to increase the volume of the microneedle tip part 59 (the objective substance), without enlarging the diameter of the microneedle 55.

Moreover, for example, in the first embodiment, with reference to the substrate 3, one penetration hole 9 is formed in one microneedle base part 7. However, it is also possible to form a plurality of penetration holes in one microneedle base part 7. In this case, during manufacturing of the microneedle array 1, it is possible that, the material 19 is injected from one of these penetration holes, and the air extraction is performed from the other penetration holes.

Moreover, in the eighth and the ninth embodiments, two grooves 83 are formed in one microneedle base part 81. However, it is also possible that, one groove 83 is formed, or three or more grooves 83 are formed, in one microneedle base part 81.

Moreover, in the eighth and the ninth embodiments, it is also possible that the microneedle base part 81 is provided with a protrusion likewise the third embodiment.

Moreover, in the second embodiment, although the projection 31 is provided on the female mold 27, it is also possible to provide a projection on the side of the substrate 3. In this case, the projection of which height is slightly lower than the base part 7 is provided appropriately around the substrate 3, so as to adjust the amount of fit-into.

Moreover, it is also possible to provide small penetration holes for the air vent, in the microneedle forming recesses of the female mold. In this case, during manufacturing of the microneedle array, the air can be extracted from the microneedle forming recesses easily. Moreover, it is also possible to form the female mold or the substrate itself by any material having the excellent gas permeability. For example, porous polyethylene, fluororesin, or polypropylene can be used. In this case, the air can be extracted from the microneedle forming recesses easily.

Moreover, in the second embodiment, the projection 31 is formed separately on the upper side of the microneedle forming recess 29 of the female mold 27. However, it is also possible to form a projection integrally with the female mold 27. Moreover, the composition of the substrate or the microneedle tip part constituting the microneedle array is not limited to the first to the ninth embodiments, and various modifications can be provided.

Example 1

Figure 22:
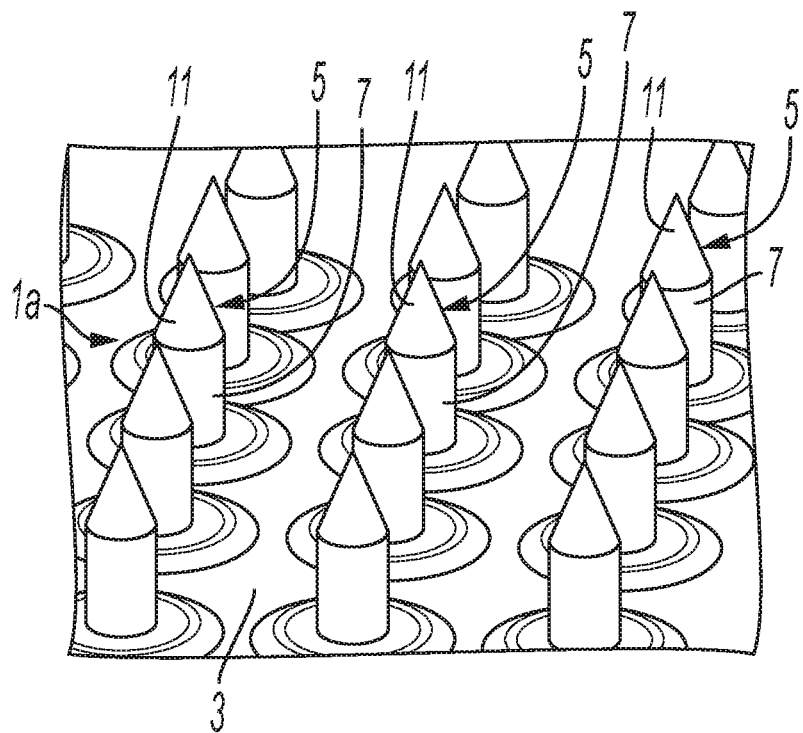
FIG. 22 A drawing showing Example 1 of the present invention, namely, an expanded photograph showing a part of a microneedle array.
Figure 23:
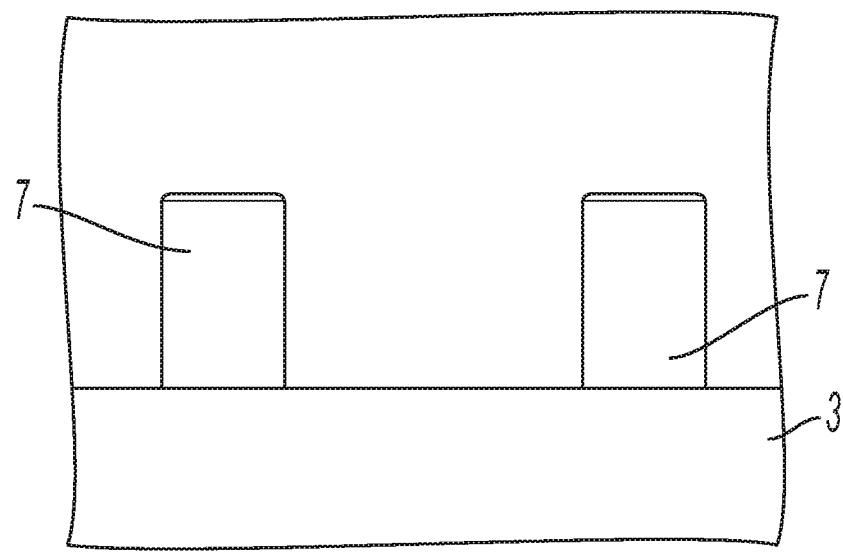
FIG. 23 A drawing showing Example 1 of the present invention, namely, an expanded photograph showing a part of a substrate of the microneedle array.

Next, Example 1 of the present invention will be explained with reference to FIG. 22 to FIG. 26. A photograph of FIG. 22 shows a microneedle array 1*a* manufactured by Example 1. Moreover, a photograph of FIG. 23 shows the substrate 3 used for the microneedle array 1*a*. As for the material of the substrate 3, PMMA (Poly Methyl Meta Acrylate resin) was used.

The microneedle array 1*a* according to Example 1 was manufactured in the method as illustrated in FIG. 8, by using the female mold 27 according to the second embodiment.

Now the detailed explanation will be made as below.

First, a mold for forming the substrate 3 provided with the microneedle base parts 7 was manufactured. The mold is made of a plate-shaped member, in which holes corresponding to the microneedle base parts 7 are formed. The holes were formed by precision drilling.

Next, the substrate 3 was formed by heat nanoimprinting molding. Namely, the a PMMA sheet, of which thickness is 1 mm, was overlapped on the side of the mold on which the holes had been formed, and under heating at the temperature of 130° C., the pressure at 10 MPa was applied for 15 minutes, whereby the substrate 3 was formed. Thereafter, after cooling the PMMA to be not more than the glass transition temperature (about 109° C.) thereof, the finished substrate 3 was removed.

Moreover, the height (the dimension in the upward/downward direction of FIG. 23) of the microneedle base part 7 formed on the substrate 3 was 507 µm, and the diameter was 304 µm.

Next, the penetration holes 9 were formed in the substrate 3. The penetration holes 9 were formed by femtosecond laser. The diameter of the penetration hole 9 was approximately 40 µm.

Figure 24:
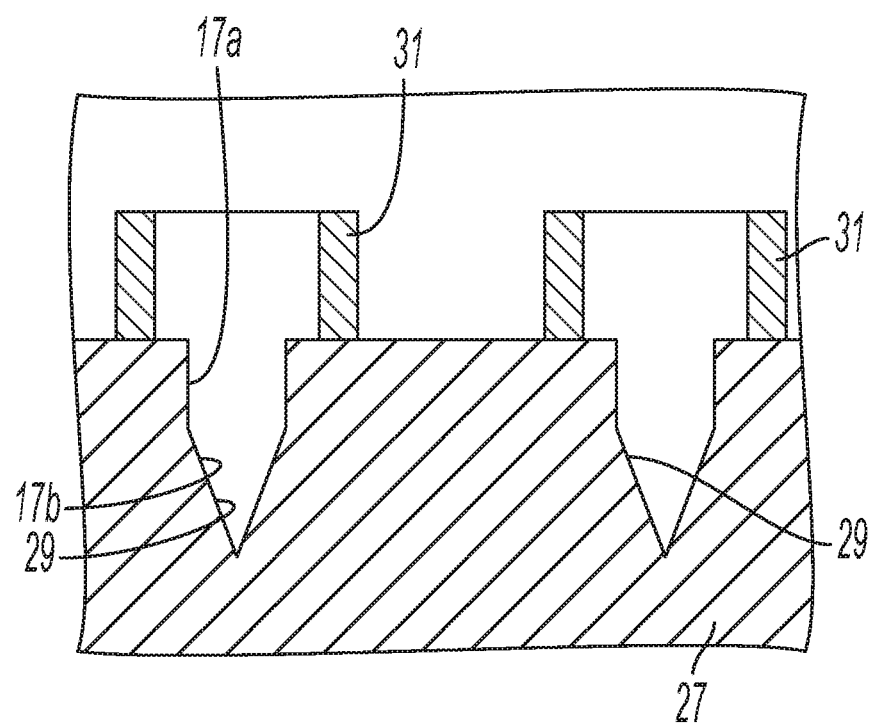
FIG. 24 A drawing showing Example 1 of the present invention, namely, an expanded photograph showing the cross section of a part of a female mold used for manufacturing of the microneedle array.

Next, the female mold 27 for forming the microneedles 5 on the top end sides of the microneedle base parts 7 of the substrate 3 was manufactured. A photograph of FIG. 24 shows the female mold 27. As described above, the female mold 27 has the microneedle forming recesses 29 formed therein. With regard to the microneedle forming recess 29, the cylindrical recess section 17*a* had 238 µm of the diameter and 490 µm of the length, and the conical recess section 17*b* had 238 µm of the diameter at the bottom surface thereof, which was the same diameter as that of the cylindrical recess section 17*a*, and 307 µm of the depth. Moreover, the projection 31 of the female mold 27 had 600 µm of the diameter and 296 µm of the height.

The female mold 27 is made of silicone rubber, which was manufactured by casting using a metal mold as described below. Using SILPOT 184 (Dow Corning), a main agent and a curing agent were mixed at the rate of 10:1, and the vacuum defoaming was performed, whereby the material for the female mold 27 was manufactured. Next, this material was casted into the metal mold. Next, heat at the temperature of 80° C. was applied thereto for 20 minutes, so as to harden the material. Thereafter, the finished female mold 27 was removed from the metal mold.

Next, by using the female mold 27, the microneedle tip parts 11 of the microneedles 5 were manufactured. First, by using a versatile dispenser, acrylic water-soluble ultraviolet curing resin TB 3046 (Three Bond, the concentration at 20%) as the material 19 was injected, for approximately 20 nl, into the microneedle forming recesses 29 of the female mold 27.

Next, the substrate 3 was fitted into the female mold 27. At that time, the surface of the substrate 3 was arranged to be in contact with the projections 31 of the female mold 27.

Figure 25:
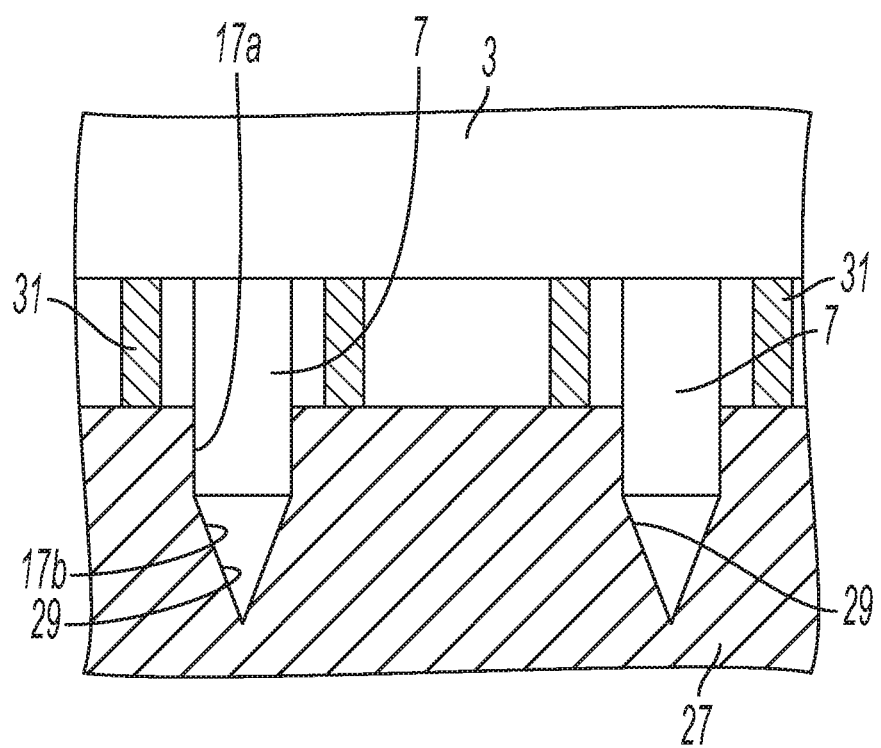
FIG. 25 A drawing showing Example 1 of the present invention, namely, an expanded photograph showing a state that the substrate of the microneedle array is fitted into the female mold used for manufacturing of the microneedle array.
Figure 26A:
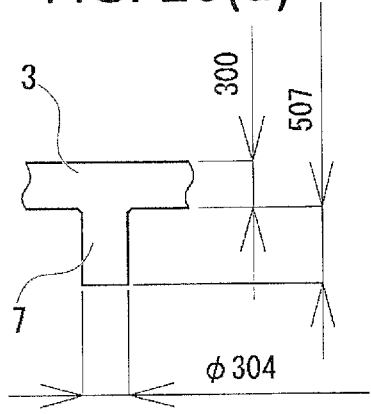
Figure 26B:
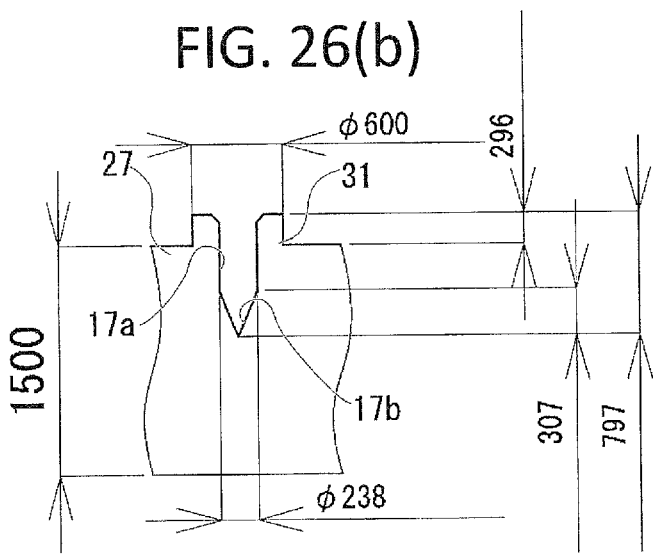
Figure 26C:
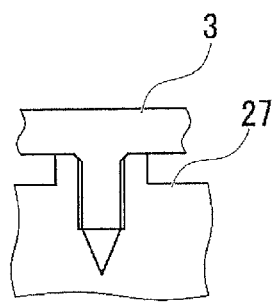
Figure 26D:
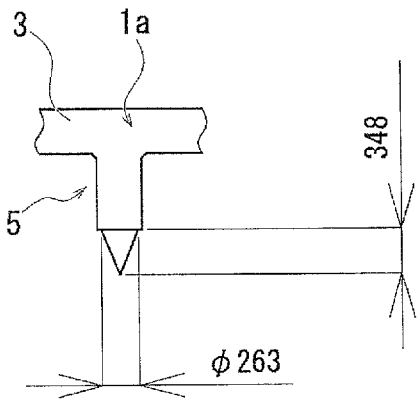

Note that, a photograph of FIG. 25 shows a state that the substrate 3 is fitted into the female mold 27, without injecting the ultraviolet curing resin as the material 19 into the microneedle forming recesses 29. This photograph shows that, with regard to the respective microneedle forming recesses 29 and the microneedle base parts 7, the center positions and the fit-into amount thereof coincide with each other.

Next, the material 19 was hardened by irradiating the ultraviolet light (40 mW, 1 min.). Thereafter, the microneedle array 1a was removed from the female mold 27. As shown in FIG. 22, the microneedle tip part 11 made of ultraviolet curing resin is installed on the top end side of the microneedle base part 7 of the microneedle array 1a. The microneedle tip part 11 in a conical shape had 263 µm of the diameter at the bottom surface thereof, and 348 µm of the height. In the case of the microneedle array 1a according to Example 1, in a square shape, 5×5=25 microneedles 5 were formed, and the pitch between the respective microneedles 5 was 1.0 mm.

The dimensions of the respective parts of the substrate 3, the female mold 27, and the microneedle array 1a as the final product, used in Example 1, are shown in FIG. 26 as a summary. FIG. 26 (*a*) is a partial view of the substrate 3, FIG. 26 (*b*) is a partial view of the female mold 27, FIG. 26 (*c*) is a partial view showing a state that the substrate 3 is fitted into the female mold 27, and FIG. 26 (*d*) is a partial view of the microneedle array 1a as the final product. First, the thickness of the substrate 3 is 300 µm, the diameter of the base part 7 is 304 µm, and the height of the base part 7 is 507 µm. Moreover, the outer diameter of the projection 31 of the female mold 27 is 600 µm, and the height thereof is 296 µm. Moreover, the inner diameter of the cylindrical recess section 17a of the female mold 27 is 238 µm. Moreover, the thickness of the female mold 27 is 1500 µm, the distance from the lower end of the cylindrical recess section 17a to the top end of the reverse-conical recess section 17b of the female mold 27 is 307 µm, and the distance from the upper end of the projection 31 to the top end of the reverse-conical recess section 17b is 797 µm. Further, with regard to the microneedle array 1a as the final product, the diameter of the microneedle tip part 11 is 263 µm, and the height of the microneedle tip part 11 is 348 µm.

Example 2

Figure 27:
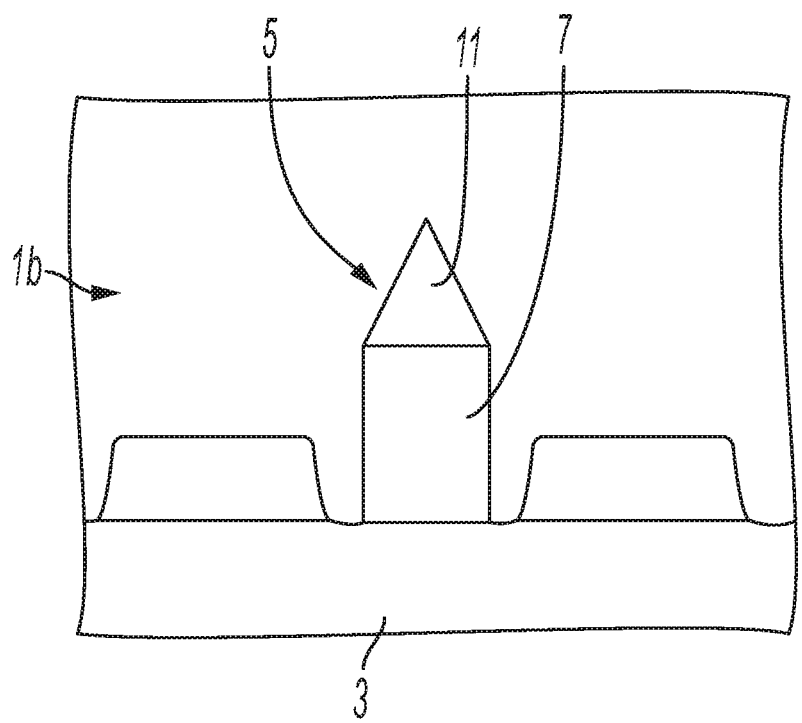
FIG. 27 A drawing showing Example 2 of the present invention, namely, an expanded photograph showing a part of a microneedle array.
Figure 28A:
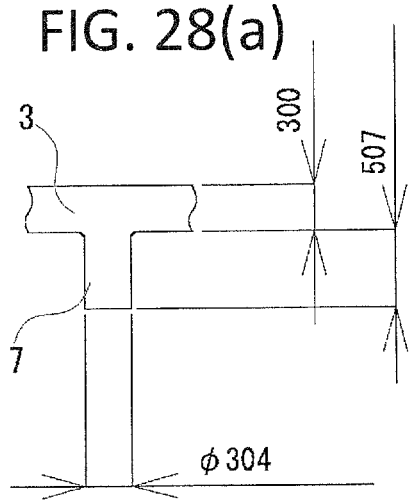
Figure 28B:
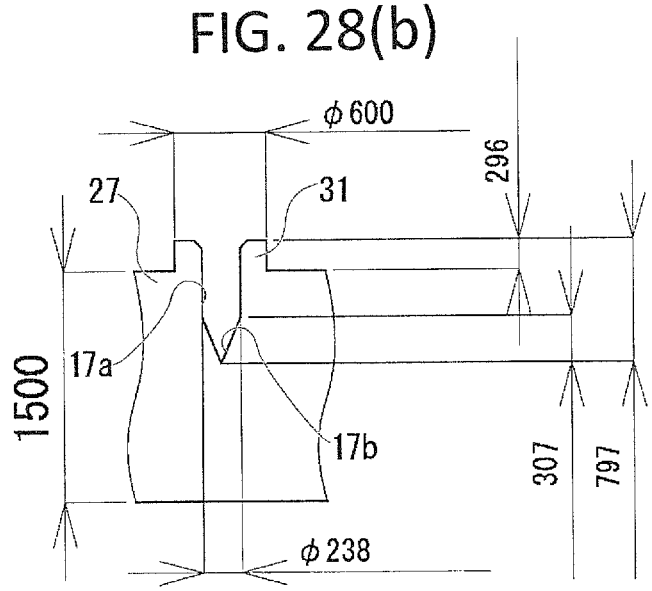
Figure 28C:
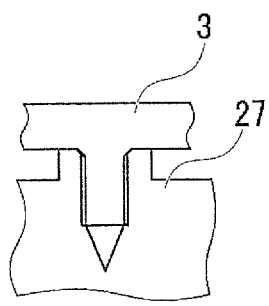
Figure 28D:
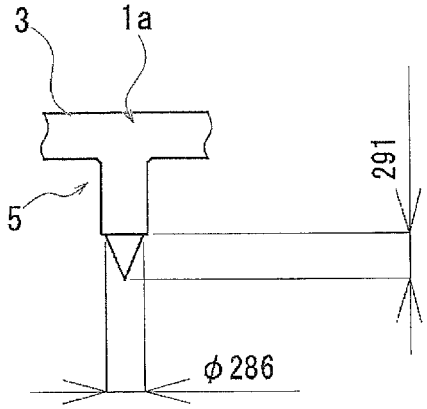

Next, Example 2 of the present invention will be explained with reference to FIG. 27 and FIG. 28. FIG. 27 shows a microneedle array 1b manufactured by Example 2. Moreover, the shape of the microneedle array 1b is substantially the same as the microneedle array 1a of Example 1.

Moreover, the microneedle array 1b according to Example 2 was also manufactured in the method as illustrated in FIG. 8, by using the female mold 27 according to the second embodiment. Now the detailed explanation will be made as below.

First, a mold for forming the substrate 3 provided with the microneedle base parts 7 was manufactured. This mold is substantially the same as the mold for forming the substrate 3 in Example 1.

Next, likewise the case of Example 1, the substrate 3 was formed by heat nanoimprinting molding. This substrate 3 is also substantially the same as that of Example 1, namely, the height (the dimension in the upward/downward direction of FIG. 27) of the microneedle base part 7 formed on the substrate 3 was 507 µm, and the diameter was 304 µm.

Next, the penetration holes 9 were formed in the substrate 3. Likewise the case of Example 1, the penetration holes 9 were formed by femtosecond laser. The diameter of the penetration hole 9 was also approximately 40 µm, which was substantially the same as Example 1.

Next, the female mold 27 for forming the microneedles 5 on the top end sides of the microneedle base parts 7 was manufactured substantially in the same method as that of Example 1. The dimensions of the female mold 27 are substantially the same as those of Example 1.

Next, by using the female mold 27, the microneedle tip parts 11 of the microneedles 5 were manufactured. First, by using a versatile dispenser, water-soluble polyvinylpyrrolidone (the concentration at 20%) as the material 19 was injected, for approximately 30 nl, into the microneedle forming recesses 29 of the female mold 27.

Next, the substrate 3 was fitted into the female mold 27. At that time, the surface of the substrate 3 was arranged to be in contact with the projections 31 of the female mold 27. Also in the case of Example 2, likewise the case of Example 1, the substrate 3 is fitted into the female mold 27. Namely, as shown in FIG. 25, with the projections 31, in regard to the respective microneedle forming recesses 29 and the microneedle base parts 7, the center positions and the fit-into amount thereof are arranged to coincide with each other.

Next, the substrate 3, the female mold 27 and the material 19 were heated on a hot plate for 30 minutes to reach 80° C., so as to harden the material 19. Thereafter, the microneedle array 1b was removed from the female mold 27. As shown in FIG. 27, the microneedle tip part 11 made of polyvinylpyrrolidone is installed on the top end side of the microneedle base part 7 of the microneedle array 1b. The tip part in a conical shape had 286 µm of the diameter at the bottom surface thereof, and 291 µm of the height. In the case of the microneedle array 1b according to Example 2, in a square shape, 5×5=25 microneedles 5 were formed, and the pitch between the respective microneedles 5 was 1.0 mm.

Note that, in FIG. 27, protrusions on the both sides of the microneedle 5 on the substrate 3 are the excess material leaked to be hardened, due to inappropriate injecting volume of the material.

The dimensions of the respective parts of the substrate 3, the female mold 27, and the microneedle array 1b as the final product, used in Example 2, are shown in FIG. 28 as a summary. FIG. 28 (*a*) is a partial view of the substrate 3, FIG. 28 (*b*) is a partial view of the female mold 27, FIG. 28 (*c*) is a partial view showing a state that the substrate 3 is fitted into the female mold 27, and FIG. 28 (*d*) is a partial view of the microneedle array 1b as the final product. First, the thickness of the substrate 3 is 300 µm, the diameter of the base part 7 is 304 µm, and the height of the base part 7 is 507 µm. Moreover, the outer diameter of the projection 31 of the female mold 27 is 600 µm, and the height thereof is 296 µm. Moreover, the inner diameter of the cylindrical recess section 17a of the female mold 27 is 238 µm. Moreover, the thickness of the female mold 27 is 1500 µm, the distance from the lower end of the cylindrical recess section 17a to the top end of the reverse-conical recess section 17b of the female mold 27 is 307 µm, and the distance from the upper end of the projection 31 to the top end of the reverse-conical recess section 17b is 797 µm. Further, with regard to the microneedle array 1b as the final product, the diameter of the microneedle tip part 11 is 286 µm, and the height of the microneedle tip part 11 is 291 µm.

Example 3

Figure 29:
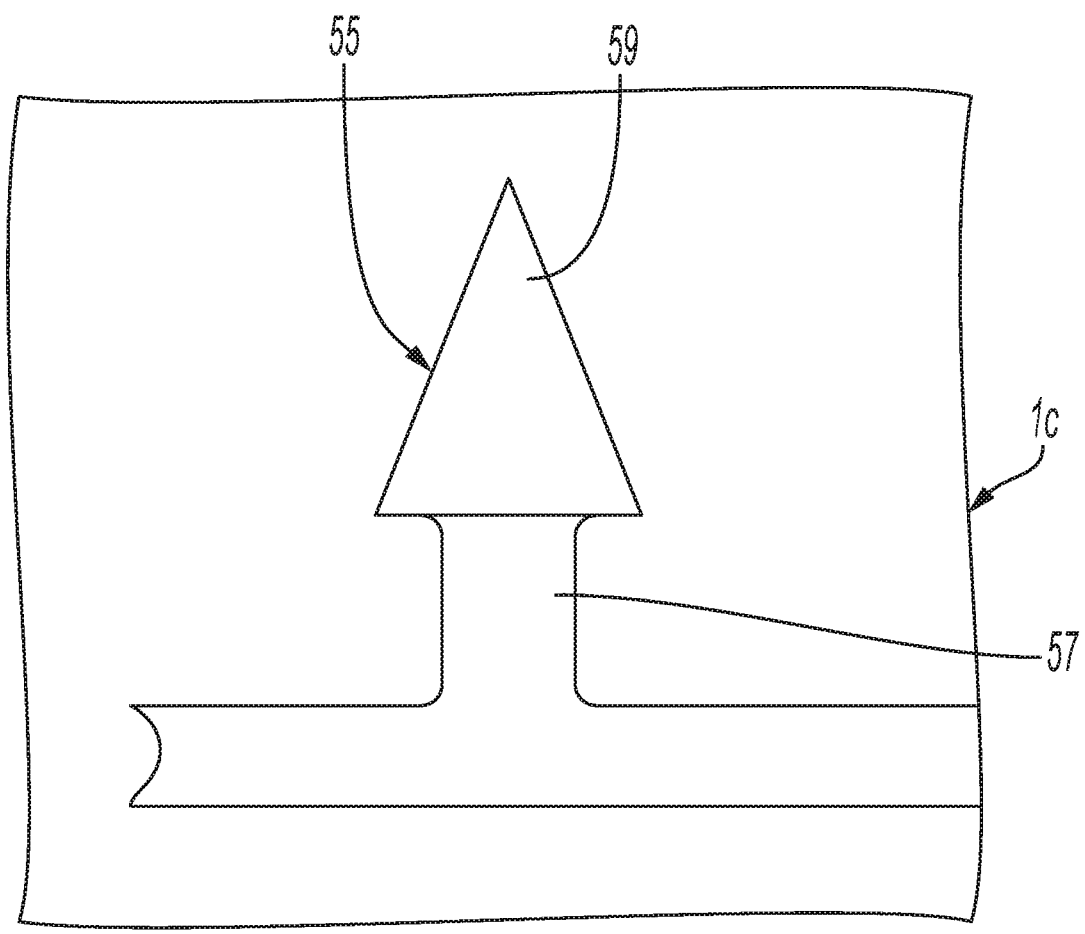
FIG. 29 A drawing showing Example 3 of the present invention, namely, an expanded photograph showing a part of a microneedle array.

Next, Example 3 of the present invention will be explained with reference to FIG. 29 to FIG. 32. FIG. 29 shows a microneedle array 1c manufactured by Example 3.

Moreover, the microneedle array 1c according to Example 3 was manufactured basically in the same method as that of Example 2, and differs only in the dimensions of the base part, the shape of the female mold, and the existence of the barb formed as a result of manufacturing. Now the detailed explanation will be made as below.

First, likewise the case of Example 2, the microneedle base parts 57 were formed by heat nanoimprinting molding. Note that, the formed microneedle base part 57 was smaller in its dimensions, than the microneedle base part 7 of Example 2 shown in FIG. 27, namely, the height was 408 µm, and the diameter was 186 µm.

Figure 30:
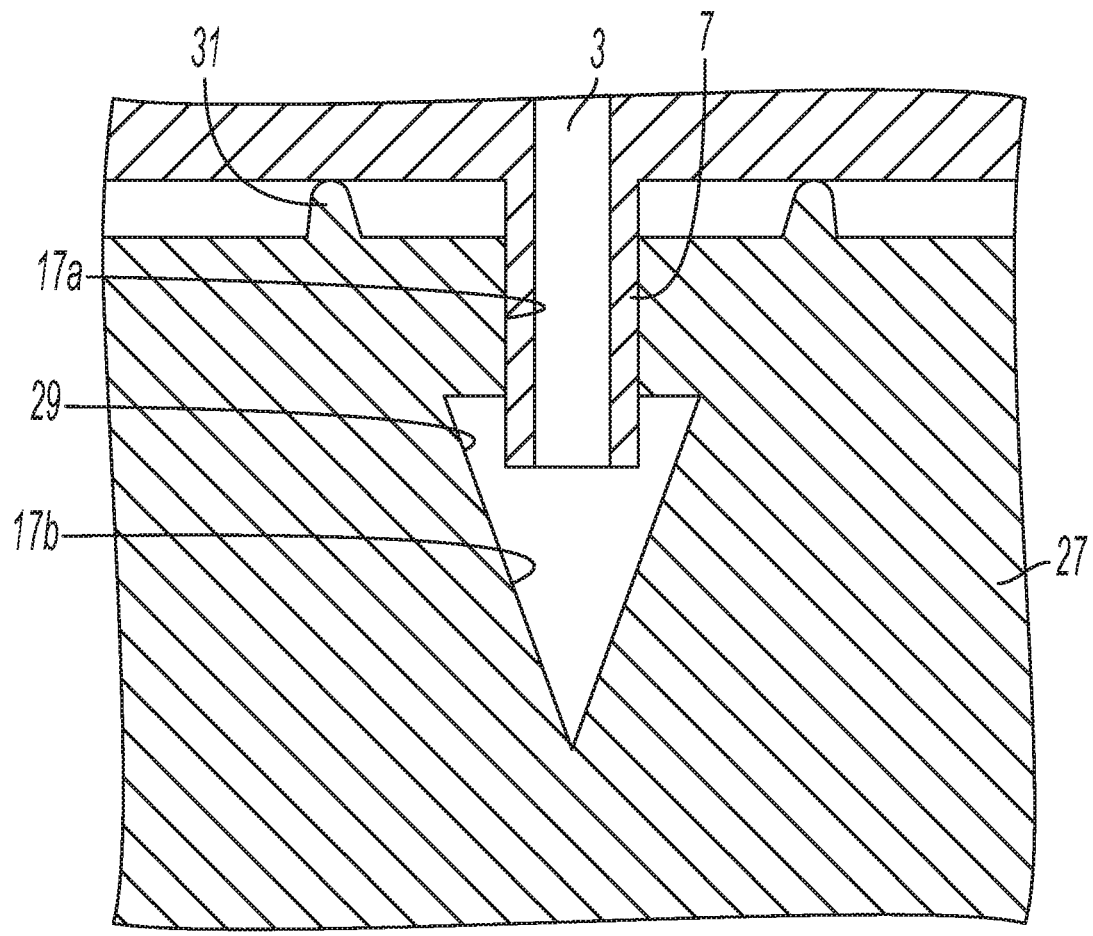
FIG. 30 A drawing showing Example 3 of the present invention, namely, an expanded photograph showing a part of a state that a substrate of the microneedle array is fitted into a female mold used for manufacturing of the microneedle array.

Next, the female mold 27 for forming the microneedles 55, each of which has a shape of barb on the top end side of the microneedle base part 57, was manufactured. This female mold 27 is shown in FIG. 30.

Note that, the manufacturing method of the female mold 27 is substantially the same as that of Example 2, except that a metal mold used therefor has a shape of barb. Moreover, the overall depth of the microneedle forming recess 29 was 780 µm, and the diameter of the cylindrical recess section 17a was 175 µm. Moreover, the diameter at the bottom surface of the conical recess section 17b was 366 µm, which was larger than those of the cylindrical recess section 17a and the microneedle base part 57. Moreover, with regard to the projection 31 of the female mold 27, the width was 50 µm, the (outer) diameter was 694 µm, and the height was 55 µm.

Next, by using the female mold 27 and the microneedle base parts 57, the microneedle tip parts 59 were manufactured substantially in the same method as that of Example 2. Namely, first, by using a versatile dispenser, water-soluble polyvinylpyrrolidone (the concentration at 20%) was injected, for approximately 25 nl, into the microneedle forming recesses 29 of the female mold 27.

Next, the substrate 3 was fitted into the female mold 27. At that time, the surface of the substrate was arranged to be in contact with the projections 31 of the female mold 27.

Note that, a photograph of FIG. 30 shows a state that the substrate 3 is fitted into the female mold 27, without injecting the polyvinylpyrrolidone as the material 19 into the microneedle forming recesses 29.

Next, likewise the case of Example 2, the substrate 3, the female mold 27 and the material 19 were heated on the hot plate for 60 minutes to reach 80° C., so as to harden the material. Thereafter, the microneedle array 1c was removed from the female mold 27. As shown in FIG. 29, the microneedle tip part 59 made of polyvinylpyrrolidone is installed on the top end side of the microneedle base part 57 of the microneedle array 1c. With regard to the tip part in a conical shape, the maximum diameter was 379 µm, and the height was 496 µm. Moreover, in this state, due to elasticity of the female mold 27, the barb-shaped parts were removed, with almost no deformation thereof, from the female mold 27.

Figure 31A:
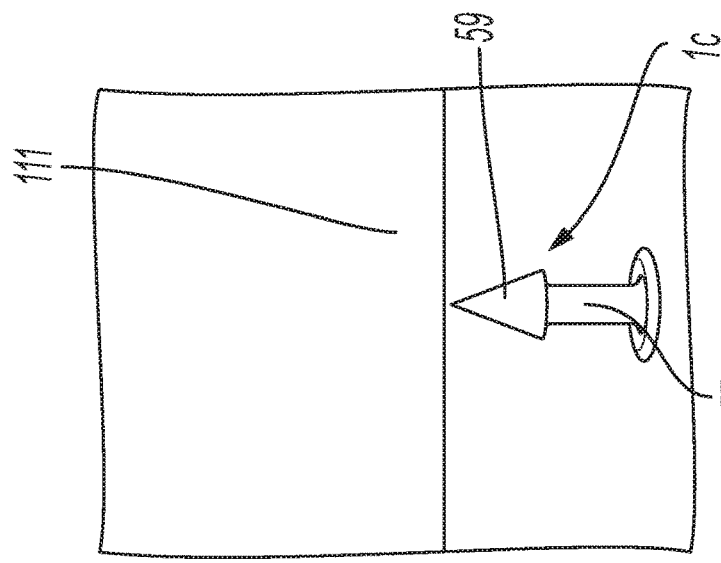
Figure 31B:
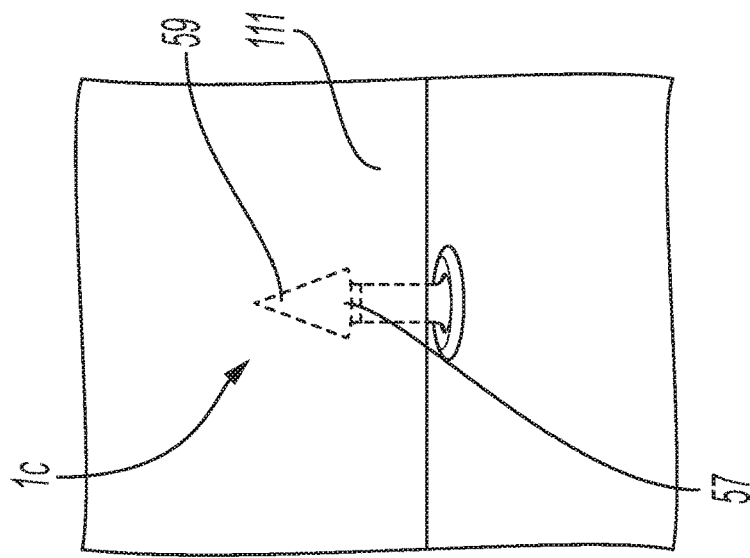
Figure 31C:
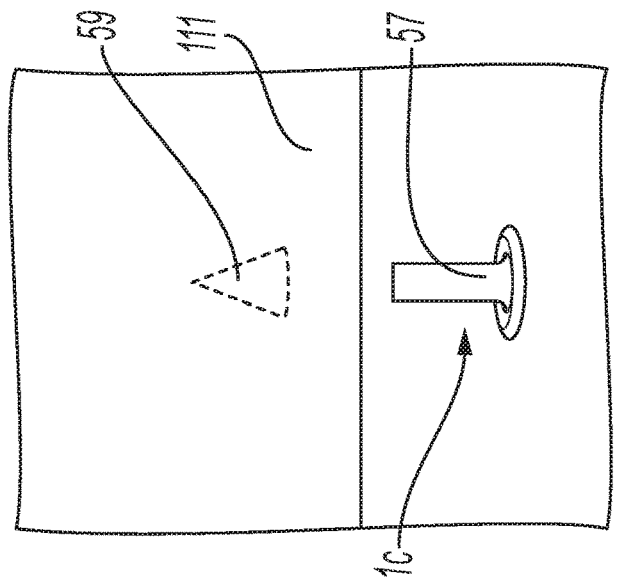
Figure 32A:
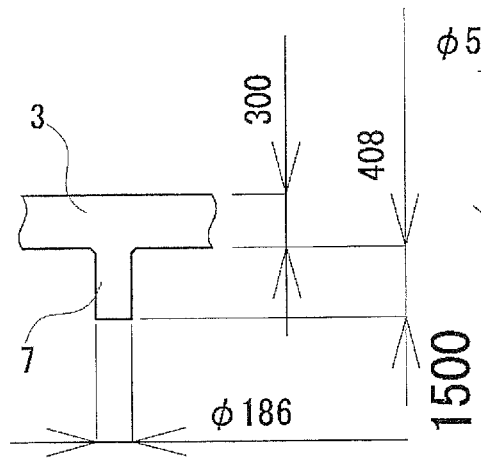
Figure 32B:
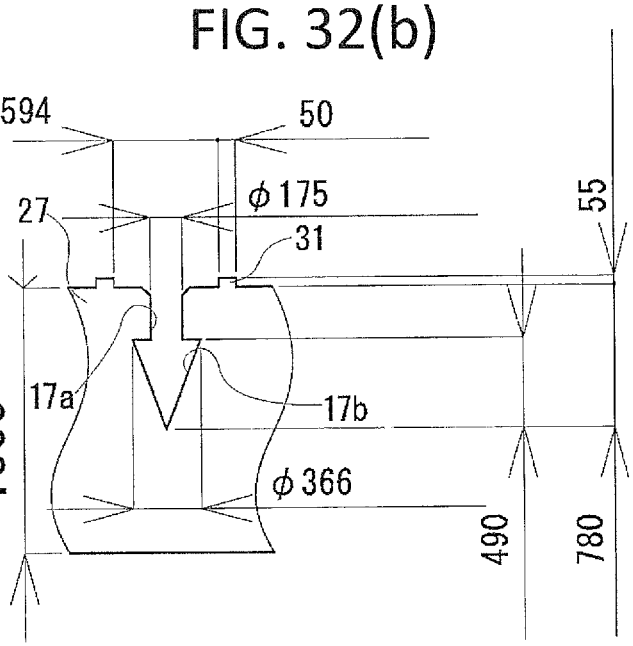
Figure 32C:
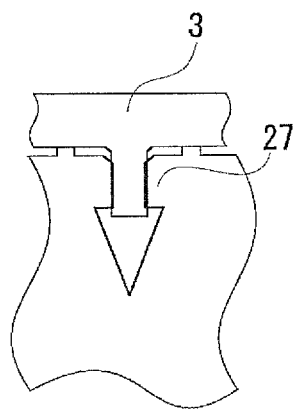
Figure 32D:
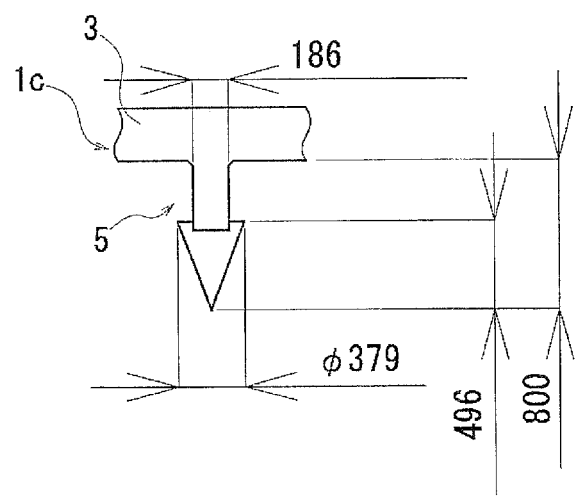
Figure 33:
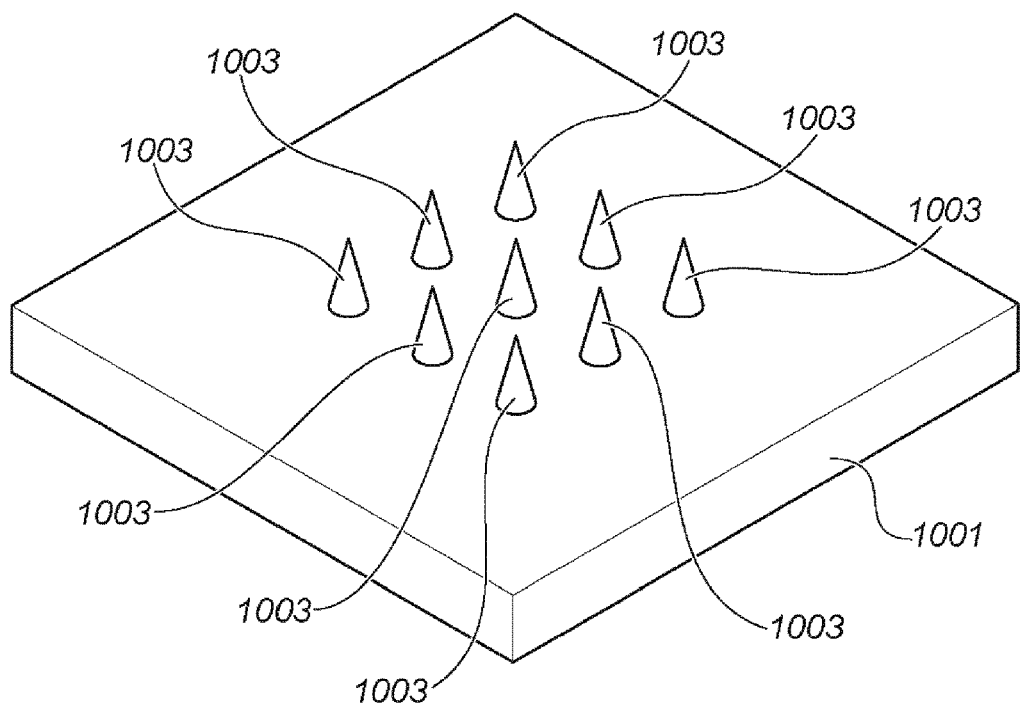
FIG. 33 A drawing showing a conventional art, namely, a perspective view of a microneedle array of a conventional art.
Figure 34:
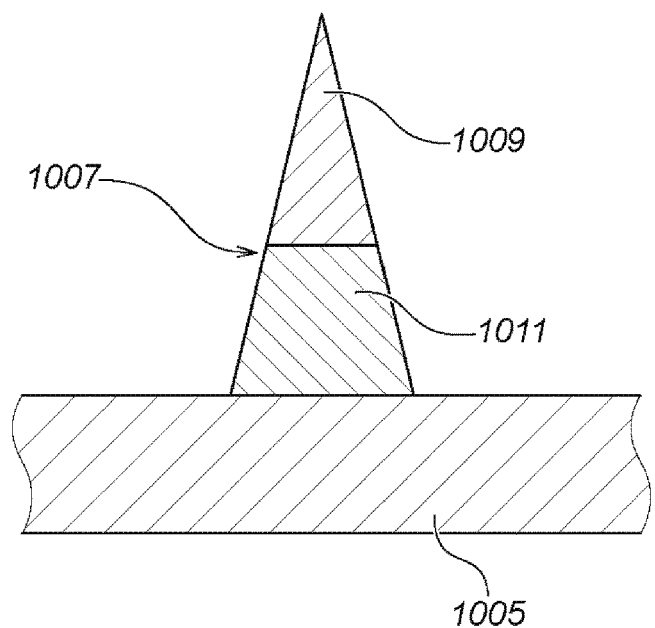
FIG. 34 A drawing showing a conventional art, namely, a partially expanded sectional view showing a part of a microneedle array of a conventional art.

Next, with the microneedle array 1c, a puncture test was executed into a silicone rubber as a dummy skin, so as to verify the puncturing strength and the effect of the barbs. First, FIG. 31 (a) shows a state before puncturing, in which, a silicone rubber sheet 111 is disposed above the microneedle array 1c. Next, FIG. 31 (b) shows a state that the microneedle array 1c was punctured perpendicularly from the lower side, toward the silicone rubber sheet 111. In this state, the microneedle array 1c was punctured into the silicone rubber sheet 111 smoothly, without falling down from the bottom nor being deformed. Next, when the microneedle array 1c was removed downwardly, it was possible that only the microneedle tip parts 59 remained in the silicone rubber sheet 111. FIG. 31 (c) shows such a state. Accordingly, it was proven that, with the barb shape, only the tip parts can remain inside the skin easily.

The dimensions of the respective parts of the substrate 3, the female mold 27, and the microneedle array 1c as the final product, used in Example 3, are shown in FIG. 32 as a summary. FIG. 32 (a) is a partial view of the substrate 3. FIG. 32 (b) is a partial view of the female mold 27, FIG. 32 (c) is a partial view showing a state that the substrate 3 is fitted into the female mold 27, and FIG. 32 (d) is a partial view of the microneedle array 1c as the final product. First, the thickness of the substrate 3 is 300 µm, the diameter of the base part 7 is 186 µm, and the height of the base part 7 is 408 µm. Moreover, the outer diameter of the projection 31 of the female mold 27 is 604 µm, the width thereof is 50 µm, and the height thereof is 55 µm. Moreover, the inner diameter of the cylindrical recess section 17a of the female mold 27 is 175 µm. Moreover, the thickness of the female mold 27 is 1500 µm, the distance from the upper end of the cylindrical recess section 17a to the top end of the reverse-conical recess section 17b of the female mold 27 is 780 µm, and the distance from the upper end of the projection 31 to the top end of the reverse-conical recess section 17b is 835 µm. Further, with regard to the microneedle array 1c as the final product, the diameter of the microneedle tip part 11 is 379 µm, and the height of the microneedle tip part 11 is 496 µm.

INDUSTRIAL APPLICABILITY

The present invention relates to a microneedle array for performing subcutaneous administration of an objective substance such as medical agent for the purposes of prevention and treatment of various diseases, and a microneedle array manufacturing method for manufacturing such a microneedle array, and more specifically, relates to that which is not easily damaged during puncturing, whereby the puncturing can be surely performed, and a desired volume of the objective substance can be surely administrated. For example, the present invention is suitable for the microneedle array for the use of subcutaneous administration of vaccines.

EXPLANATION OF REFERENCE NUMERALS AND SIGNS 1, 1a, 1b Microneedle Array
3 Substrate
5 Microneedle 7 Microneedle Base Part
9 Penetration Hole (Microneedle Tip Part Intrusion Recess)
11 Microneedle Tip Part
13 Projection
15 Female Mold
17 Microneedle Forming Recess
19 Material (Serving as Microneedle Tip Part after solidified)
21 Skin
23 Jig
25 Projection
27 Female Mold
29 Microneedle Forming Recess
31 Projection
37 Microneedle Array
39 Substrate
41 Microneedle
42 Microneedle Base Part
43 Protrusion
45 Microneedle Tip Part
47 Recess
49 Projection
51 Microneedle Array
53 Substrate
55 Microneedle
57 Microneedle Base Part
58 Protrusion
59 Microneedle Tip Part
60 Perpendicular Part
61 Recess
63 Projection
65 Microneedle Array
67 Uneven Part
68 Microneedle Array
69 Microneedle Array
71 Substrate
73 Microneedle
75 Microneedle Base Part
77 Microneedle Tip Part
79 Substrate
81 Microneedle Base Part
83 Groove (Microneedle Tip Part Intrusion Recess)
85 Female Mold
87 Microneedle Forming Recess
89 Groove (Passage)
91 Female Mold
93 Microneedle Forming Recess
95 Projection
97 Groove (Passage)
99 Substrate
101 Penetration Hole (Passage)
103 Female Mold
105 Microneedle Forming Recess
107 Groove (Passage)

The invention claimed is:

1. A microneedle array manufacturing method, comprising the steps of:
preparing a female mold provided with microneedle forming recesses, and also preparing a substrate having an integrally formed plurality of microneedle base parts protruding from a first side of the substrate, each of the plurality of microneedle base parts being provided with a penetration hole as a microneedle tip part intrusion recess formed therein;
fitting the plurality of microneedle base parts into the microneedle forming recesses, respectively;
after the step of fitting, filling a dissolved or melted material, constituting a microneedle tip part and containing an objective substance, in each of the microneedle forming recesses from a second side of the substrate opposite to the first side, so as to allow intrusion of a part of a filling material into each of the penetration holes as the microneedle tip part intrusion recesses; and
removing, after expiration of a predetermined curing, the substrate from the female mold, so as to obtain the microneedle array, having the microneedle tip part installed on top of each of the plurality of the microneedle base parts of the substrate.

2. The microneedle array manufacturing method as claimed in claim 1, wherein the microneedle base part is fitted into the microneedle forming recess under laminar flow, in a direction perpendicular to the laminar flow.

3. The microneedle array manufacturing method as claimed in claim 1, wherein dimensions of the microneedle tip part are controlled with adjustment of fitting amount of the microneedle base part into the microneedle forming recess.

4. The microneedle array manufacturing method as claimed in claim 1, wherein the female mold is made of an elastomer material.

5. The microneedle array manufacturing method as claimed in claim 1, wherein a projection is provided on an edge of the microneedle forming recess of the female mold.

6. The microneedle array manufacturing method as claimed in claim 1, wherein passages are formed in the female mold and the substrate for communicating the microneedle forming recesses with outside.

7. The microneedle array manufacturing method as claimed in claim 1,
wherein in the step of preparing, each of the microneedle forming recesses is formed to include
a first recess section to receive the microneedle base part, and
a second recess section extending from the first recess section and having a shape in which a cross-sectional area thereof reduces in a direction away from the first recess section to form the microneedle tip part,
in the step of fitting, the plurality of microneedle base parts fits into the first recess sections, respectively,
in the step of filling, the dissolved or melted material enters each of the second recess sections through the penetration hole, and the part of the filled material remains in each of the penetration holes, and
in the step of removing, the microneedle tip part is formed on the top of each of the plurality of the microneedle base parts of the substrate and a projection extending from the microneedle tip part toward the second side of the substrate is formed in each of the penetration holes.

8. A microneedle array manufacturing method, comprising the steps of:
preparing a female mold provided with microneedle forming recesses, and also preparing a substrate having an integrally formed plurality of microneedle base parts protruding from a first side of the substrate, each of the plurality of microneedle base parts being provided with a penetration hole or a groove as a microneedle tip part intrusion recess formed therein;
fitting the plurality of microneedle base parts into the microneedle forming recesses, respectively;
after the step of fitting, filling a dissolved or melted material constituting microneedle tip parts and containing an objective substance, in each of the microneedle forming recesses from a second side of the substrate opposite to the first side, so as to allow intrusion of a part of a filled filling material into each of the penetration holes or grooves as the microneedle tip part intrusion recesses; and removing, after expiration of a predetermined curing, the substrate from the female mold, so as to obtain the microneedle array, having the microneedle tip part installed on top of each of the plurality of the microneedle base parts of the substrate.

* * * * *